(12) United States Patent     (10) Patent No.: US 8,048,454 B2
Martin     (45) Date of Patent: Nov. 1, 2011

(54) METHODS AND COMPOSITIONS RELATED TO REGULATION OF CYTOKINE PRODUCTION BY GLYCOGEN SYNTHASE KINASE 3 (GSK-3)

(76) Inventor: Michael Martin, Crestwood, KY (US)

( * ) Notice: Subject to any disclaimer, the term of this patent is extended or adjusted under 35 U.S.C. 154(b) by 866 days.

(21) Appl. No.: 10/598,671

(22) PCT Filed: Mar. 9, 2005

(86) PCT No.: PCT/US2005/007586
§ 371 (c)(1),
(2), (4) Date: Sep. 7, 2006

(87) PCT Pub. No.: WO2005/086814
PCT Pub. Date: Sep. 22, 2005

(65) Prior Publication Data
US 2008/0175923 A1     Jul. 24, 2008

Related U.S. Application Data

(60) Provisional application No. 60/551,646, filed on Mar. 9, 2004.

(51) Int. Cl.
   *A61K 33/14*     (2006.01)
   *A61K 33/00*     (2006.01)
   *A61P 43/00*     (2006.01)
   *A61P 31/04*     (2006.01)
(52) U.S. Cl. ............... 424/677; 424/722; 514/921
(58) Field of Classification Search ............... 424/677, 424/722; 514/886, 921
See application file for complete search history.

(56) References Cited

U.S. PATENT DOCUMENTS

| 4,386,072 A | 5/1983 | Horrobin et al. |
| 6,441,053 B1 | 8/2002 | Klein et al. |
| 2005/0075276 A1 | 4/2005 | Rudd |

FOREIGN PATENT DOCUMENTS

| WO | WO 98/17288 | | 4/1998 |
| WO | WO 00/38675 | * | 7/2000 |

OTHER PUBLICATIONS

Medline abstract, accession No. 1983257030 (1990).*
Bagshawe, K.D., "The First Bagshawe lecture. Towards generating cytotoxic agents at cancer sites" Br. J. Cancer, 60:275-281, (1989).
Bagshawe, et al., "A cytotoxic agent can be generated selectively at cancer sites" Br. J. Cancer, 58:700-703, (1988).
Battelli, et al., "T lymphocyte killing by a xanthine-oxidase-containing immunotoxin" Cancer Immunol. Immunother., 35:421-425, (1992).
Berg, D. J., K. Kuhn, K. Rajewsky, W. Muller, S. Menon, N. Davidson, G. Grunig, and D. Rennick 1995. Interleukin-10 is a central regulator of the response to LPS in murine models of endotoxic shock and the Shwartzman reaction but not endotoxin tolerance J. Clin. Invest. 96:2339-2347.
Brigham et al., "Expression of a prokaryotic gene in cultured lung endothelial cells after lipofection with a plasmid vector" Am. J. Resp. Cell. Mol. Biol. 1:95 100 (1989).
Brown and Greene, "Molecular and cellular mechanisms of receptor-mediated endocytosis" DNA and Cell Biology 10:6, 399-409 (1991).
Cichon (2001) "Complement activation by recombinant adenoviruses" Gene Ther 8:1794-1800.
Cohen (2002) "The immunopathogenesis of sepsis" Nature 420(6917):885-91.
Cohen, "The role of protein phosphorylation in human health and disease" Eur. J. Biochem. 268:5001-5010 (2001).
Cross, D. A., D. R. Alessi, P. Cohen, M. Andjelkovich, and B. A. Hemmings 1995. Inhibition of glycogen synthase kinase-3 by insulin mediated by protein kinase B Nature. 378:785-789.
Cross, D. A., A. A. Culbert, K. A. Chalmers, L. Facci, S. D. Skaper, and A. D. Reith 2001. Selective small-molecule inhibitors of glycogen synthase kinase-3 activity protect primary neurones from death J. Neurochem. 77:94-102.
Demarchi et al., "Gas6 anti-apoptotic signaling requires NF-kappaB activation" J. Biol. Chem. 276:31738-31744 (2001).
Demarchi et al., "Glycogen synthase kinase-3 beta regulates NF-kappaB1/p105 stability" J. Biol. Chem. 278:39583-90 (2003).
Doble and Woodgett "GSK-3: trickes of the trade for a multi-tasking kinase" J. Cell Sci. 116:1175-86 (2003).
Dinarello, C. A. 2000. "Proinflammatory cytokines" Chest. 118:503-508.
Feghali et al., "Cytokines in acute and chronic inflammation" Frontiers in Bioscience 2, d12-26, Jan. 1, 1997.
Franke, T. F., D. R. Kaplan, L. C. Cantley, and A. Toker 1997. Direct regulation of the Akt proto-oncogene product by phosphatidylinositol-3,4-bisphosphate Science. 275:665-668.
Fukao, T., M. Tanabe, Y. Terauchi, T. Ota, S. Matsuda, T. Asano, T. Kadowaki, T. Takeuchi, and S. Koyasu 2002. PI3K-mediated negative feedback regulation of IL-12 production in DCs Nat. Immunol. 3:875-881.
Fukao, T., T. Yamada, M. Tanabe, Y. Terauchi, T. Ota, T. Takayama, T. Asano, T. Takeuchi, T. Kadowaki, J. J. Hata, and S. Koyasu 2002. Selective loss of gastrointestinal mast cells and impaired immunity in PI3K-deficient mice. Nat Immunol. 3:295-304.
Ghosh et al., "NF-kappaB and rel proteins: evolutionary conserved mediators of immune responses" Annu. Rev. Immunol. 16:225-260 (1998).
Grimes and Jope "CREB DNA binding activity is inhibited by glycogen synthase kinase-3 beta and facilitated by lithium" J. Neurochem. 78:1219-1232 (2001).
Guha, M., and N. Mackman 2002. The phosphatidylinositol 3-kinase-Akt pathway limits lipopolysaccharide activation of signaling pathways and expression of inflammatory mediators in human monocytic cells J. Biol. Chem. 277:32124-32132.
Han, S. H., J. H. Kim, M. Martin, S. M. Michalek, and M. H. Nahm 2003. Pneumococcal lipoteichoic acid (LTA) is not as potent as staphylococcal LTA in stimulating Toll-like receptor 2 Infect. Immun. 71:5541-5548.
Hirschfeld, M., Y. Ma, J. H. Weis, S. N. Vogel, and J. J. Weis 2000. Cutting edge: repurification of lipopolysaccharide eliminates signaling through both human and murine toll-like receptor 2 J. Immunol. 165:618-622.

(Continued)

*Primary Examiner* — John Pak
(74) *Attorney, Agent, or Firm* — C. Allen Black

(57) ABSTRACT

This invention relates generally to a method of treating inflammation and associated diseases and disorders by administering an agent that inhibits glycogen synthase kinase 3 activity.

13 Claims, 13 Drawing Sheets

OTHER PUBLICATIONS

Hirschfeld, M., J. J. Weis, V. Toshchakov, C. A. Salkowski, M. J. Cody, D. C. Ward, N. Qureshi, S. M. Michalek, and S. N. Vogel 2001. Signaling by Toll-like receptor 2 and 4 agonists results in differential gene expression in murine macrophages Infect. Immun. 69:1477-1482.

Hoeflich et al., "Requirement for glycogen synthase kinase-3 beta in cell survival and NF-kappaB activation" Nature 406:86-90 (2000).

Howard, M., T. Muchamuel, S. Andrade, and S. Menon 1993. Interleukin 10 protects mice from lethal endotoxemia J. Exp. Med. 177:1205-1208.

Jooss, K. (2003) "Immunity to adenovirus and adeno-associated viral vectors: implications for gene therapy" Gene Ther. 10:955-963.

Kim et al., "Glycogen synthase kinase 3beta is a natural activator of mitogen-activated protein kinase/extracellular signal-regulated kinase kinase kinase 1 (MEKK1)" *Journal of Biological Chemistry* 278(16):13995-14001 (2003).

Klein and Melton "A molecular mechanism for the effect of lithium on development" PNAS 93:8455-59 (1996).

Kunick et al., "1-Azakenpaullone is a selective inhibitor of glycogen synthase kinase-3 beta" Bioorg. Med. Chem. Lett. 19:413-6 (2004).

Lawlor, M. A., and D. R. Alessi 2001. PKB/Akt: a key mediator of cell proliferation, survival and insulin responses? J. Cell. Sci. 114:2903-2910.

Martin, M., R. E. Schifferle, N. Cuesta, S. N. Vogel, J. Katz, and S. M. Michalek 2003. Role of the phosphatidylinositol 3 kinase-Akt pathway in the regulation of IL-10 and IL-12 by Porphyromonas gingivalis lipopolysaccharide J. Immunol. 171:717-725.

Meijer et al., "GSK-3 selective inhibitors derived from Tyrian purple indirubins" Chem. Biol. 10:1255-66 (2003).

Morton et al., "A reinvestigation of the multisite phosphorylation of the transcription factor c-Jun" *EMBO Journal* 22(15):3876-3886 (2003).

Nemeth et al., "Lithium induces NF-kappaB activation and interleukin-8 production in human intestinal epithelial cells" J. Biol. Chem. 277:7713-9 (2002).

O'Neill, L. A., and C. A. Dinarello 2000. The IL-1 receptor/toll-like receptor superfamily: crucial receptors for inflammation and host defense Immunol. Today. 21:206-209.

Parker et al., "Phosphorylation of CREB at Ser-133 induces complex formation with CREB-binding protein via a direct mechanism" Mol. Cell Biol. 16:694-703 (1996).

Parry and Mackman "Role of cyclic AMP response element binding protein in cyclic AMP inhibition of NV-kappaB-mediated mechanism" J. Immunol. 159:5450-6 (1997).

Pietersz and McKenzie, "Antibody conjugates for the treatment of cancer" Immunolog. Reviews, 129:57-80, (1992).

Platzer et al., "Cyclic adenosine monophosphate-responsive elements are involved in the transcriptional activation of the human IL-10 gene in monocytic cells" Eur. J. Immunol. 29:3098-3104 (1999).

Roffler, et al., "Anti-neoplastic glucuronide prodrug treatment of human tumor cells targeted with a monoclonal antibody-enzyme conjugate" Biochem. Pharmacol, 42:2062-2065, (1991).

Schwabe and Brenner "Role of glycogen synthase kinase-3 in TNF-alpha-induced NF-kappaB activation and apoptosis in hepatocytes" Am. J. Physiol. Gastrointest. Liver Physiol. 283:G204-G211 (2002).

Senter, et al., "Generation of 5-fluorouracil from 5-fluorocytosine by monoclonal antibody-cytosine deaminase conjugates" Bioconjugate Chem., 2:447-451, (1991).

Senter, et al., "Generation of cytotoxic agents by targeted enzymes" Bioconjugate Chem., 4:3-9, (1993).

Sheppard et al., "Transcriptional activation by NF-kappaB requires multiple coactivators" Mol. Cell Biol. 19:6367-6378 (1999).

Stambolic et al., "Lithium inhibits glycogen synthase kinase-3 activity and mimics wingless signaling in intact cells" *Curr. Biol.* 6:1664-1668 (1996).

Stokoe, D. L. R., L. R. Stephens, T. Copeland, R. Piers, J. Gaffney, C. B. Reese, G. F. Painter, A. B. Holmes, F. McCormick, and P. T. Hawkins 1997. Dual role of phosphatidylinositol-3,4,5-trisphosphate in the activation of protein kinase B Science. 277:567-570.

Tapping, R. I., S. Akashi, K. Miyake, P. J. Godowski, and P. S. Tobias 2000. Toll-like receptor 4, but not Toll-like receptor 2, is a signaling receptor for *Escherichia* and *Salmonella* lipopolysaccharides J. Immunol. 165:5780-5787.

Walport, M.J. (2001) "Complement. First of two parts" N Eng J Med 344:1058-1066.

Walport, M.J. (2001) "Complement. Second of two parts." N Eng J Med 344:1140-1144.

Zaiss, A.K. (2002) "Differential activation of innate immune responses by adenovirus and adeno-associated virus vectors" J. Virol. 76:4580-4590.

Zhong et al., "Phosphorylation of NF-kappaB p65 by PKA stimulates transcriptional activity by promoting a novel bivalent interaction with the coactivator CBP/p300" Mol. Cell 1:661-671 (1998).

\* cited by examiner

D

SEQUENCE LISTING

```
<160> NUMBER OF SEQ ID NOS: 6

<210> SEQ ID NO 1
<211> LENGTH: 483
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 1

Met Ser Gly Gly Gly Pro Ser Gly Gly Gly Pro Gly Gly Ser Gly Arg
1               5                   10                  15

Ala Arg Thr Ser Ser Phe Ala Glu Pro Gly Gly Gly Gly Gly Gly Gly
                20                  25                  30

Gly Gly Gly Pro Gly Gly Ser Ala Ser Gly Pro Gly Gly Thr Gly Gly
            35                  40                  45

Gly Lys Ala Ser Val Gly Ala Met Gly Gly Gly Val Gly Ala Ser Ser
        50                  55                  60

Ser Gly Gly Pro Gly Gly Ser Gly Gly Gly Ser Gly Gly Pro
65                  70                  75                  80

Gly Ala Gly Thr Ser Phe Pro Pro Pro Gly Val Lys Leu Gly Arg Asp
                85                  90                  95

Ser Gly Lys Val Thr Thr Val Val Ala Thr Leu Gly Gln Gly Pro Glu
                100                 105                 110

Arg Ser Gln Glu Val Ala Tyr Thr Asp Ile Lys Val Ile Gly Asn Gly
            115                 120                 125

Ser Phe Gly Val Val Tyr Gln Ala Arg Leu Ala Glu Thr Arg Glu Leu
        130                 135                 140

Val Ala Ile Lys Lys Val Leu Gln Asp Lys Arg Phe Lys Asn Arg Glu
145                 150                 155                 160

Leu Gln Ile Met Arg Lys Leu Asp His Cys Asn Ile Val Arg Leu Arg
                165                 170                 175

Tyr Phe Phe Tyr Ser Ser Gly Glu Lys Lys Asp Glu Leu Tyr Leu Asn
                180                 185                 190

Leu Val Leu Glu Tyr Val Pro Glu Thr Val Tyr Arg Val Ala Arg His
            195                 200                 205

Phe Thr Lys Ala Lys Leu Thr Ile Pro Ile Leu Tyr Val Lys Val Tyr
        210                 215                 220

Met Tyr Gln Leu Phe Arg Ser Leu Ala Tyr Ile His Ser Gln Gly Val
225                 230                 235                 240

Cys His Arg Asp Ile Lys Pro Gln Asn Leu Leu Val Asp Pro Asp Thr
                245                 250                 255

Ala Val Leu Lys Leu Cys Asp Phe Gly Ser Ala Lys Gln Leu Val Arg
```

-continued

```
                        260                 265                 270
Gly Glu Pro Asn Val Ser Tyr Ile Cys Ser Arg Tyr Tyr Arg Ala Pro
            275                 280                 285
Glu Leu Ile Phe Gly Ala Thr Asp Tyr Thr Ser Ile Asp Val Trp
        290                 295                 300
Ser Ala Gly Cys Val Leu Ala Glu Leu Leu Leu Gly Gln Pro Ile Phe
305                 310                 315                 320
Pro Gly Asp Ser Gly Val Asp Gln Leu Val Glu Ile Ile Lys Val Leu
                325                 330                 335
Gly Thr Pro Thr Arg Glu Gln Ile Arg Glu Met Asn Pro Asn Tyr Thr
            340                 345                 350
Glu Phe Lys Phe Pro Gln Ile Lys Ala His Pro Trp Thr Lys Val Phe
            355                 360                 365
Lys Ser Arg Thr Pro Pro Glu Ala Ile Ala Leu Cys Ser Ser Leu Leu
        370                 375                 380
Glu Tyr Thr Pro Ser Ser Arg Leu Ser Pro Leu Glu Ala Cys Ala His
385                 390                 395                 400
Ser Phe Phe Asp Glu Leu Arg Cys Leu Gly Thr Gln Leu Pro Asn Asn
                405                 410                 415
Arg Pro Leu Pro Pro Leu Phe Asn Phe Ser Ala Gly Glu Leu Ser Ile
            420                 425                 430
Gln Pro Ser Leu Asn Ala Ile Leu Ile Pro Pro His Leu Arg Ser Pro
            435                 440                 445
Ala Gly Thr Thr Thr Leu Thr Pro Ser Ser Gln Ala Leu Thr Glu Thr
        450                 455                 460
Pro Thr Ser Ser Asp Trp Gln Ser Thr Asp Ala Thr Pro Thr Leu Thr
465                 470                 475                 480
Asn Ser Ser

<210> SEQ ID NO 2
<211> LENGTH: 420
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 2

Met Ser Gly Arg Pro Arg Thr Thr Ser Phe Ala Glu Ser Cys Lys Pro
1               5                   10                  15
Val Gln Gln Pro Ser Ala Phe Gly Ser Met Lys Val Ser Arg Asp Lys
            20                  25                  30
Asp Gly Ser Lys Val Thr Thr Val Val Ala Thr Pro Gly Gln Gly Pro
        35                  40                  45
Asp Arg Pro Gln Glu Val Ser Tyr Thr Asp Thr Lys Val Ile Gly Asn
    50                  55                  60
Gly Ser Phe Gly Val Val Tyr Gln Ala Lys Leu Cys Asp Ser Gly Glu
65                  70                  75                  80
Leu Val Ala Ile Lys Lys Val Leu Gln Asp Lys Arg Phe Lys Asn Arg
                85                  90                  95
Glu Leu Gln Ile Met Arg Lys Leu Asp His Cys Asn Ile Val Arg Leu
            100                 105                 110
Arg Tyr Phe Phe Tyr Ser Ser Gly Glu Lys Lys Asp Glu Val Tyr Leu
        115                 120                 125
Asn Leu Val Leu Asp Tyr Val Pro Glu Thr Val Tyr Arg Val Ala Arg
    130                 135                 140
```

His Tyr Ser Arg Ala Lys Gln Thr Leu Pro Val Ile Tyr Val Lys Leu
145                 150                 155                 160

Tyr Met Tyr Gln Leu Phe Arg Ser Leu Ala Tyr Ile His Ser Phe Gly
                165                 170                 175

Ile Cys His Arg Asp Ile Lys Pro Gln Asn Leu Leu Leu Asp Pro Asp
            180                 185                 190

Thr Ala Val Leu Lys Leu Cys Asp Phe Gly Ser Ala Lys Gln Leu Val
        195                 200                 205

Arg Gly Glu Pro Asn Val Ser Tyr Ile Cys Ser Arg Tyr Tyr Arg Ala
    210                 215                 220

Pro Glu Leu Ile Phe Gly Ala Thr Asp Tyr Thr Ser Ser Ile Asp Val
225                 230                 235                 240

Trp Ser Ala Gly Cys Val Leu Ala Glu Leu Leu Leu Gly Gln Pro Ile
                245                 250                 255

Phe Pro Gly Asp Ser Gly Val Asp Gln Leu Val Glu Ile Ile Lys Val
            260                 265                 270

Leu Gly Thr Pro Thr Arg Glu Gln Ile Arg Glu Met Asn Pro Asn Tyr
        275                 280                 285

Thr Glu Phe Lys Phe Pro Gln Ile Lys Ala His Pro Trp Thr Lys Val
    290                 295                 300

Phe Arg Pro Arg Thr Pro Pro Glu Ala Ile Ala Leu Cys Ser Arg Leu
305                 310                 315                 320

Leu Glu Tyr Thr Pro Thr Ala Arg Leu Thr Pro Leu Glu Ala Cys Ala
                325                 330                 335

His Ser Phe Phe Asp Glu Leu Arg Asp Pro Asn Val Lys Leu Pro Asn
            340                 345                 350

Gly Arg Asp Thr Pro Ala Leu Phe Asn Phe Thr Thr Gln Glu Leu Ser
        355                 360                 365

Ser Asn Pro Pro Leu Ala Thr Ile Leu Ile Pro Pro His Ala Arg Ile
    370                 375                 380

Gln Ala Ala Ala Ser Pro Pro Ala Asn Ala Thr Ala Ala Ser Asp Thr
385                 390                 395                 400

Asn Ala Gly Asp Arg Gly Gln Thr Asn Asn Ala Ala Ser Ala Ser Ala
                405                 410                 415

Ser Asn Ser Thr
            420

<210> SEQ ID NO 3
<211> LENGTH: 2189
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 3
gcggcgcggc ctggaagagg ccagggcccg ggggaggcgg cggcagcggc ggcggctggg      60
gcagcccggg cagcccgagc cccgcagcct gggcctgtgc tcggcgccat gagcggcggc     120
gggccttcgg gaggcggccc tgggggctcg ggcagggcgc ggactagctc gttgcgggag     180
cccggcggcg gaggcggagg aggcggcggc ggccccggag gctcggcctc cggcccaggc     240
ggcaccggcg gcggaaaggc atctgtcggg gccatgggtg ggggcgtcgg ggcctcgagc     300 tccggggtg gacccggcgg cagcggcgga ggaggcagcg gaggcccgg cgcaggcact      360 agcttcccgc cgcccggggt gaagctgggc cgtgacagcg ggaaggtgac cacagtcgta     420

-continued

```
gccactctag gccaaggccc agagcgctcc caagaagtgg cttacacgga catcaaagtg      480
attggcaatg gctcatttgg ggtcgtgtac caggcacggc tggcagagac cagggaacta      540
gtcgccatca agaaggttct ccaggacaag aggttcaaga accgagagct gcagatcatg      600
cgtaagctgg accactgcaa tattgtgagg ctgagatact ttttctactc cagtggcgag      660
aagaaagacg agctttacct aaatctggtg ctggaatatg tgcccgagac agtgtaccgg      720
gtggcccgcc acttcaccaa ggccaagttg accatccta tcctctatgt caaggtgtac       780
atgtaccagc tcttccgcag cttggcctac atccactccc agggcgtgtg tcaccgcgac      840
atcaagcccc agaacctgct ggtggaccct gacactgctg tcctcaagct ctgcgatttt      900
ggcagtgcaa agcagttggt ccgaggggag cccaatgtct cctacatctg ttctcgctac      960
taccgggccc cagagctcat ctttggagcc actgattaca cctcatccat cgatgtttgg     1020
tcagctggct gtgtactggc agagctcctc ttgggccagc ccatcttccc tggggacagt     1080
ggggtggacc agctggtgga gatcatcaag gtgctgggaa caccaacccg ggaacaaatc     1140
cgagagatga accccaacta cacggagttc aagttccctc agattaaagc tcaccctgg      1200 acaaaggtgt tcaaatctcg aacgccgcca gaggccatcg cgctctgctc tagcctgctg     1260
gagtacaccc catcctcaag gctctccca ctagaggcct gtgcgcacag cttcttgat       1320 gaactgcgat gtctgggaac ccagctgcct aacaaccgcc cacttccccc tctcttcaac     1380
ttcagtgctg gtgaactctc catccaaccg tctctcaacg ccattctcat ccctcctcac     1440
ttgaggtccc cagcgggcac taccaccctc acccgtcct cacaagcttt aactgagact      1500
ccgaccagct cagactggca gtcgaccgat gccacaccta ccctcactaa ctcctcctga    1560
gggccccacc aagcacccctt ccacttccat ctgggagccc caagaggggc tgggaagggg    1620
ggccatagcc catcaagctc ctgccctggc tgggccccta gactagagggg cagaggtaaa    1680 tgagtccctg tccccacctc cagtccctcc ctcaccagcc tcacccctgt ggtgggcttt     1740
ttaagaggat tttaactggt tgtggggagg gaagagaagg acagggtgtt gggggatga      1800 ggacctccta cccccttggc cccctccccct ccccagacc tccacctcct ccagaccccc     1860
tcccctcctg tgtcccttgt aaatagaacc agccagccc gtctcctctt cccttccctg      1920
gcccccgggt gtaaatagat tgttataatt ttttttcttaa agaaaacgtc gattcgcacc    1980
gtccaacctg gccccgcccc tcctacagct gtaactcccc tcctgtcctc tgcccccaag    2040
gtctactccc tcctcacccc accctggagg gccaggggag tggagagagc tcctgatgtc    2100
ttagtttcca cagtaaggtt tgcctgtgta cagacctccg ttcaataaat tattggcatg     2160
aaaacctgaa aaaaaaaaaa aaaaaaaa                                         2189
```

<210> SEQ ID NO 4
<211> LENGTH: 1639
<212> TYPE: DNA
<213> ORGANISM: Artificial Sequence
<220> FEATURE:
<223> OTHER INFORMATION: Description of Artificial Sequence; note = synthetic construct

<400> SEQUENCE: 4

```
atcatctata tgttaaatat ccgtgccgat ctgtcttgaa ggagaaatat atcgcttgtt       60 ttgttttta tagtatacaa aaggagtgaa aagccaagag gacgaagtct ttttctttt        120 cttctgtggg agaacttaat gctgcattta tcgttaacct aacaccccaa cataaagaca      180
aaaggaagaa aaggaggaag gaaggaaaag gtgattcgcg aagagagtga tcatgtcagg     240
gcggcccaga accacctcct ttgcggagag ctgcaagccg gtgcagcagc cttcagcttt     300
```

```
tggcagcatg aaagttagca gagacaagga cggcagcaag gtgacaacag tggtggcaac    360
tcctgggcag ggtccagaca ggccacaaga agtcagctat acagacacta aagtgattgg    420
aaatggatca tttggtgtgg tatatcaagc caaactttgt gattcaggag aactggtcgc    480
catcaagaaa gtattgcagg acaagagatt taagaatcga gagctccaga tcatgagaaa    540
gctagatcac tgtaacatag tccgattgcg ttatttcttc tactccagtg gtgagaagaa    600
agatgaggtc tatcttaatc tggtgctgga ctatgttccg gaaacagtat acagagttgc    660
cagacactat agtcgagcca aacagacgct ccctgtgatt tatgtcaagt tgtatatgta    720
tcagctgttc cgaagtttag cctatatcca ttcctttgga atctgccatc gggatattaa    780
accgcagaac ctcttgttgg atcctgatac tgctgtatta aaactctgtg actttggaag    840
tgcaaagcag ctggtccgag gagaacccaa tgtttcgtat atctgttctc ggtactatag    900
ggcaccagag ttgatctttg gagccactga ttatacctct agtatagatg tatggtctgc    960
tggctgtgtg ttggctgagc tgttactagg acaaccaata tttccagggg atagtggtgt   1020
ggatcagttg gtagaaataa tcaaggtcct gggaactcca acaagggagc aaatcagaga   1080
aatgaaccca aactacacag aatttaaatt ccctcaaatt aaggcacatc cttggactaa   1140
ggattcgtca ggaacaggac atttcacctc aggagtgcgg gtcttccgac cccgaactcc   1200
accggaggca attgcactgt gtagccgtct gctggagtat acaccaactg cccgactaac   1260
accactggaa gcttgtgcac attcattttt tgatgaatta cgggacccaa atgtcaaact   1320
accaaatggg cgagacacac ctgcactctt caacttcacc actcaagaac tgtcaagtaa   1380
tccacctctg gctaccatcc ttattcctcc tcatgctcgg attcaagcag ctgcttcaac   1440
ccccacaaat gccacagcag cgtcagatgc taatactgga gaccgtggac agaccaataa   1500
tgctgcttct gcatcagctt ccaactccac ctgaacagtc ccgagcagcc agctgcacag   1560
gaaaaaccac cagttacttg agtgtcactc agcaacactg gtcacgtttg gaaagaatat   1620
taaaaaaaaa aaaaaaaaa                                                1639

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 5
gggggacgat cgtcggggg                                                   20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 6
gggggagcat gctgcggggg                                                  20
```

METHODS AND COMPOSITIONS RELATED TO REGULATION OF CYTOKINE PRODUCTION BY GLYCOGEN SYNTHASE KINASE 3 (GSK-3)

This application is a 371 of PCT/US05/07586, filed on Mar. 9, 2005, which claims benefit of U.S. Provisional application 60/551,646, filed on Mar. 9, 2004.

BACKGROUND OF THE INVENTION

1. Field of the Invention

This invention relates generally to a method of controlling the inflammatory response. The invention has broad applicability in inflammatory diseases or processes to control or alter inflammation.

2. Background Art

Inflammation is a complex stereotypical reaction of the body expressing the response to damage of cells and vascularized tissues. The discovery of the detailed processes of inflammation has revealed a close relationship between inflammation and the immune response. The main features of the inflammatory response are vasodilation, i.e. widening of the blood vessels to increase the blood flow to the infected area; increased vascular permeability, which allows diffusible components to enter the site; cellular infiltration by chemotaxis, or the directed movement of inflammatory cells through the walls of blood vessels into the site of injury; changes in biosynthetic, metabolic, and catabolic profiles of many organs; and activation of cells of the immune system as well as of complex enzymatic systems of blood plasma.

There are two forms of inflammation, acute and chronic. Acute inflammation can be divided into several phases. The earliest, gross event of an inflammatory response is temporary vasoconstriction, i.e. narrowing of blood vessels caused by contraction of smooth muscle in the vessel walls, which can be seen as blanching (whitening) of the skin. This is followed by several phases that occur over minutes, hours and days later. The first is the acute vascular response, which follows within seconds of the tissue injury and lasts for several minutes. This results from vasodilation and increased capillary permeability due to alterations in the vascular endothelium, which leads to increased blood flow (hyperemia) that causes redness (erythema) and the entry of fluid into the tissues (edema).

The acute vascular response can be followed by an acute cellular response, which takes place over the next few hours. The hallmark of this phase is the appearance of granulocytes, particularly neutrophils, in the tissues. These cells first attach themselves to the endothelial cells within the blood vessels (margination) and then cross into the surrounding tissue (diapedesis). During this phase erythrocytes may also leak into the tissues and a hemorrhage can occur. If the vessel is damaged, fibrinogen and fibronectin are deposited at the site of injury, platelets aggregate and become activated, and the red cells stack together in what are called "rouleau" to help stop bleeding and aid clot formation. The dead and dying cells contribute to pus formation. If the damage is sufficiently severe, a chronic cellular response may follow over the next few days. A characteristic of this phase of inflammation is the appearance of a mononuclear cell infiltrate composed of macrophages and lymphocytes. The macrophages are involved in microbial killing, in clearing up cellular and tissue debris, and in remodeling of tissues.

Chronic inflammation is an inflammatory response of prolonged duration—weeks, months, or even indefinitely—whose extended time course is provoked by persistence of the causative stimulus to inflammation in the tissue. The inflammatory process inevitably causes tissue damage and is accompanied by simultaneous attempts at healing and repair. The exact nature, extent and time course of chronic inflammation is variable, and depends on a balance between the causative agent and the attempts of the body to remove it. Etiological agents producing chronic inflammation include: (i) infectious organisms that can avoid or resist host defenses and so persist in the tissue for a prolonged period. Examples include *Mycobacterium tuberculosis*, Actinomycetes, and numerous fungi, protozoa and metazoal parasites. Such organisms are in general able to avoid phagocytosis or survive within phagocytic cells, and tend not to produce toxins causing acute tissue damage. (ii) Infectious organisms that are not innately resistant but persist in damaged regions where they are protected from host defenses. An example is bacteria which grow in the pus within an undrained abscess cavity, where they are protected both from host immunity and from blood-borne therapeutic agents, e.g. antibiotics. Some locations are particularly prone to chronic abscess formation, e.g. bone, and pleural cavities. (iii) Irritant non-living foreign material that cannot be removed by enzymatic breakdown or phagocytosis. Examples include a wide range of materials implanted into wounds (wood splinters, grit, metals and plastics), inhaled (silica dust and other particles or fibers), or deliberately introduced (surgical prostheses, sutures, etc.) Also included are transplants. Dead tissue components that cannot be broken down may have similar effects, e.g. keratin squames from a ruptured epidermoid cyst or fragments of dead bone (sequestrum) in osteomyelitis. (iv) In some cases the stimulus to chronic inflammation may be a normal tissue component. This occurs in inflammatory diseases where the disease process is initiated and maintained because of an abnormality in the regulation of the body's immune response to its own tissues—the so-called auto-immune diseases. (v) For many diseases characterized by a chronic inflammatory pathological process the underlying cause remains unknown. An example is Crohn's disease.

Examples of chronic inflammatory diseases include tuberculosis, chronic cholecystitis, bronchiectasis, rheumatoid arthritis, Hashimoto's thyroiditis, inflammatory bowel disease (ulcerative colitis and Crohn's disease), silicosis and other pneumoconiosis, and implanted foreign body in a wound.

Activation of innate immunity and promotion of inflammation are common responses to replication incompetent adenoviruses (Ad) now being developed as vectors for gene therapy (Jooss, K. (2003) Gene Ther. 10:955-963; Zaiss, A. K. (2002) J. Virol. 76:4580-4590). The complement system is central to both innate immunity and inflammation (Walport, M. J. (2001) N Eng J Med 344:1058-1066 and 1140-1144). Because it is comprised of multiple membrane-bound and blood factors, the complement system is of particular relevance in delivery of vectors administered intravenously. In fact, Cichon et al. showed complement was activated in a majority of human plasma samples when challenged with different adenoviral serotypes; complement activation was completely dependent on anti-Ad antibody (Cichon (2001) Gene Ther 8:1794-1800).

The complement mediated inactivation is a multistep enzymatic cascade which finally results in formation of a membrane attack complex (MAC) mediating the perforation of membranes and subsequent lysis of the invading organism. It is either initiated by antigen-antibody complexes (classical pathway) or via an antibody independent pathway which is activated by certain particular polysaccharides, viruses and bacteria (alternative pathway).

Human organs and cells themselves are protected to complement mediated lysis. This protection is achieved by expression of complement inactivation factors. So far, five human factors are known. CD35 (CR1) is released from the cells and acts mainly extrinsically. In contrast, CD59, CD46 (MCP), CD55 (DAF) and HRF are integrated into the cellular membrane. CD46 (MCP) is a classical transmembrane protein while HRF, CD59 and CD55 are GPI-anchored. These factors can interrupt the complement cascade at two different stages: DAF, CR1 and MCP act at an early stage of both the alternative and the classical pathway. In contrast, CD59 and HRF inhibit the assembly of the membrane attack complex, which is the final step of both pathways resulting in channel formation and lysis.

The early pro-inflammatory cascade can be initiated by endotoxin (also known as lipopolysaccharide, or LPS). LPS is one of the major constituents of the cell walls of gram-negative bacteria. Recognition of conserved microbial products, such as LPS, by the innate immune system leads to a variety of signal transduction pathways. These signal transduction pathways mediate the induction and secretion of cytokines that can regulate the level and duration of an inflammatory response. The systemic inflammatory response that accompanies endotoxic shock (caused by triggers such as the presence of LPS) is controlled by the levels of pro- and anti-inflammatory cytokines. Although the production of pro-inflammatory cytokines by cells of the innate immune system play an important role in mediating the initial host defense against invading pathogens (O'Neill, 2000), an inability to regulate the nature or duration of the host's inflammatory response can often mediate detrimental host effects as observed in chronic inflammatory diseases. Additionally, in the early stages of sepsis, the host's inflammatory response is believed to be in a hyperactive state with a predominant increase in the production of pro-inflammatory cytokines that mediate host tissue injury and lethal shock (Cohen, 2002). In this regard, the ability to suppress pro-inflammatory cytokines and/or enhance anti-inflammatory cytokines, i.e. IL-10, has been shown to severely reduce the toxic effects of endotoxin (Berg, 1995; Howard, 1993).

Past studies have identified that the phosphatidylinositol 3-kinase (PI3K) pathway can limit the production of TNF-α and IL-12 upon TLR-stimulation (Fukao, 2002; Fukao, 2002; Guha, 2002). Moreover, it has been demonstrated that the utilization of the PI3K pathway by a TLR2-agonist resulted in enhanced IL-10 production whereas the levels of IL-12 were reduced (Martin, 2003).

However, there remains a distinct need in the art for methods and compositions capable of regulating cytokine production, thereby controlling inflammation and associated disorders.

SUMMARY OF THE INVENTION

In accordance with the purpose(s) of this invention, as embodied and broadly described herein, this invention, in one aspect, relates to a method of reducing the severity of inflammation in a subject.

In another aspect, the invention relates to a method of reducing the severity of inflammation in a biological system.

In yet another aspect, the invention relates to a method of reducing the risk of inflammation in a recipient of an implantation or transplantation.

In yet another aspect, the invention relates to a composition used in the methods described herein.

BRIEF DESCRIPTION OF THE DRAWINGS

The accompanying drawings, which are incorporated in and constitute a part of this specification, illustrate embodiments of the invention and together with the description, serve to explain the principles of the invention.

(denoted LPS+SB216763) or vehicle (denoted LPS group) were given 150 μg of LPS by i.p., injection. *** indicates statistically significant differences at P<0.001, as compared to LPS-treated group. Results represent the mean±SD of 10 mice/group.

Figure 6:
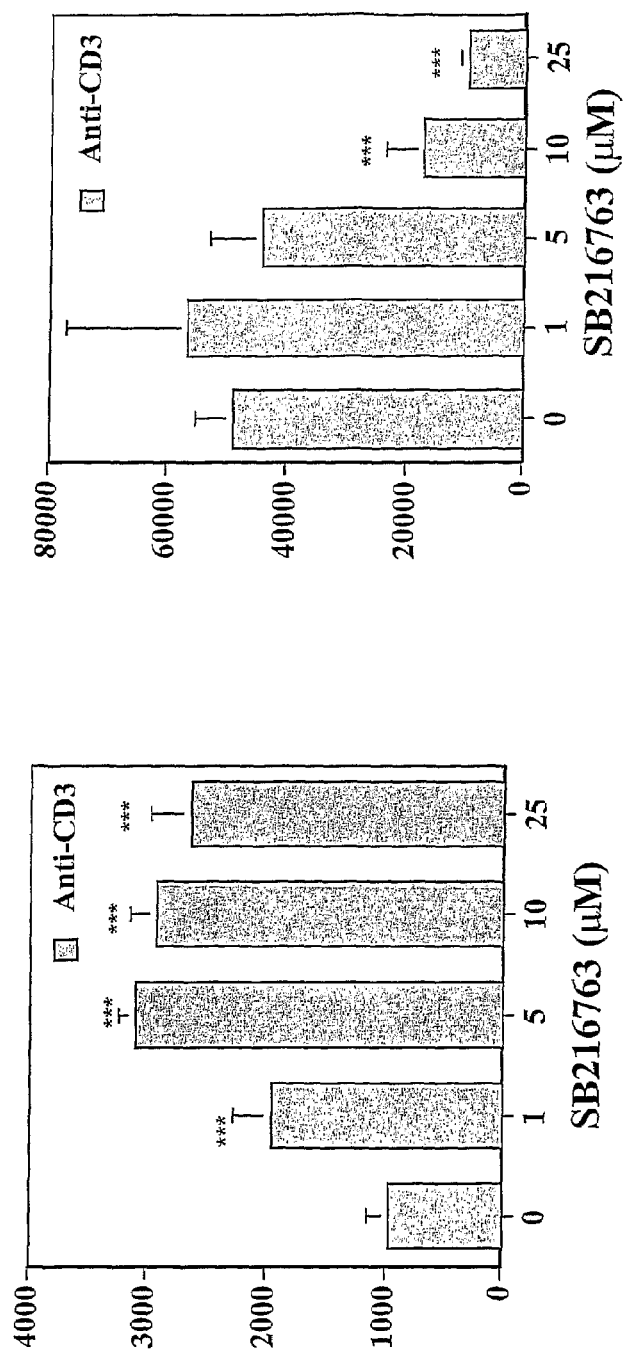

FIG. 6 shows purified human CD4$^+$ T cells were stimulated with plate-bound anti-CD3 (10 μg/ml) for 72 h in the presence of absence of the GSK-3 inhibitor SB216763. Supernatants were analyzed for Th2- (IFN-γ) and Th2- (IL-10) type cytokines by ELISA. Data demonstrates that inhibition of GSK-3 can suppress the production of inflammatory type cytokines, i.e. IFN-γ, whereas the levels of anti-inflammatory cytokines, i.e. IL-10, are significantly enhanced. *** indicates statistical significance at P<0.001, as compared to anti-CD3 stimulated T cells in the absence of GSK-3 inhibition. Thus, inhibition of GSK-3 at the T cell level also suppresses inflammatory cytokines while increasing anti-inflammatory cytokine production. Moreover, inhibition of GSK-3 can enhance Th2-type immune responses while suppressing Th1-type responses.

Figure 7:
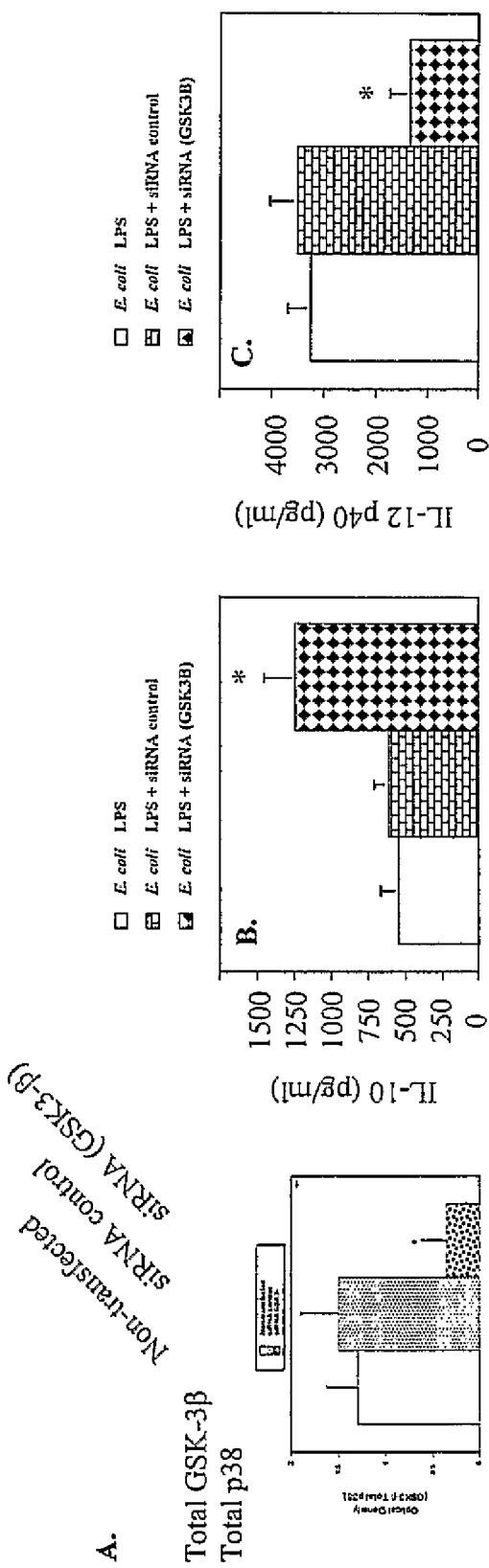

FIG. 7 shows siRNA targeting of GSK-3β demonstrates that GSK-3β is mediating a differential effect on the production of IL-10 and IL-12 p40 by *E. coli* LPS (1 μg/ml) stimulated monocytes. (A) Monocytes were pre-treated for 96 h with medium, siRNA targeting GSK-3β, or control siRNA and assayed by Western blot for the levels of total GSK-3β and total p38. (B, C) Monocytes were pre-treated with medium only, siRNA control, or siRNA targeting GSK-3β for 96 h, stimulated with *E. coli* LPS for 20 h, and cell-free supernatants assayed by ELISA for the levels of (B) IL-10 and (C) IL-12 p40. * indicates significant differences (P<0.05) compared to LPS stimulated cultures. Results represent the mean±SD of 3 separate experiments.

Figure 8:
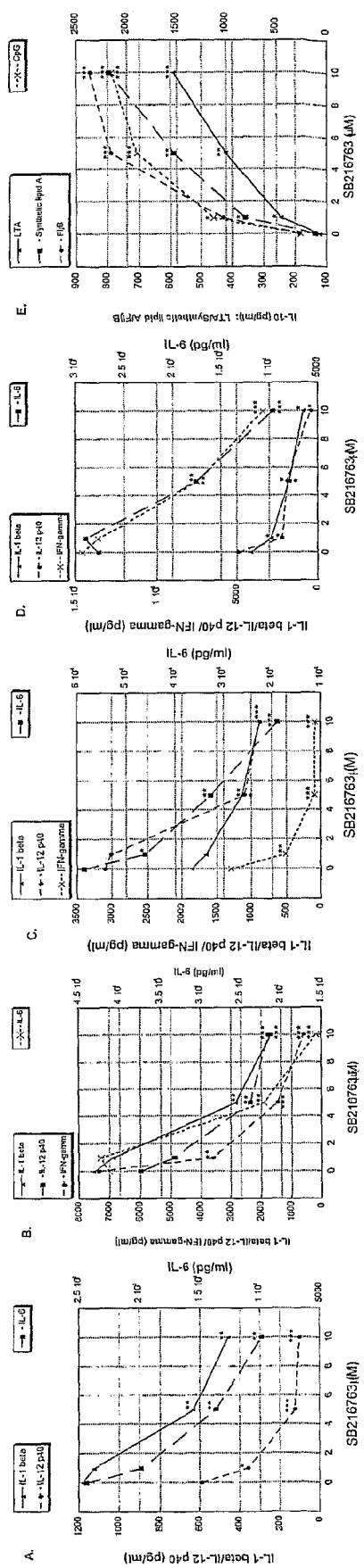

FIG. 8 shows inhibition of GSK-3 differentially regulates the levels of pro-inflammatory and anti-inflammatory cytokine production upon TLR2-, TLR4-, TLR5-, and TLR9-stimulation of human PBMC. Human PBMC were pre-treated with the indicated concentrations of SB216763 for 1 h before the addition of a (A, E) TLR2- (LTA at 10 μg/ml), (B, E) TLR4- (*E. coli* synthetic lipid A at 1 μg/ml), (C, E) TLR5- (FljB at 5 μg/ml), or (D, E) TLR9- (human CpG at 5 μM) agonist for 20 h. The levels of IL-1β, IFN-γ, IL-12 p40, IL-6, and IL-10 were determined by ELISA. Stimulation of human PBMC with LTA from *S. pneumoniae* did not result in any detectable level of IFN-γ. *,  and * indicate statistical significance at P<0.05, P<0.01, and P<0.001, respectively, as compared to TLR-treated controls containing 0.01% DMSO. Results represent the mean±SD of 5 separate experiments.

Figure 9:
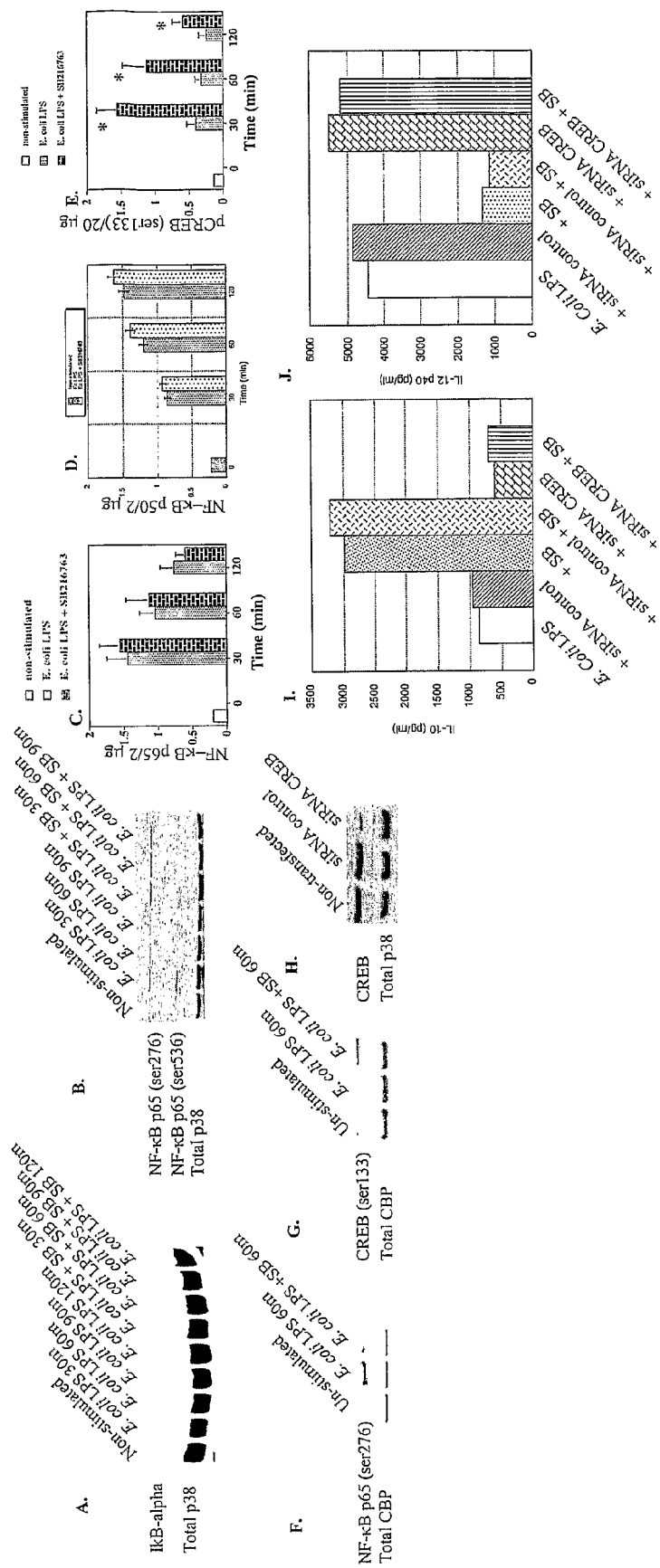

FIG. 9 shows GSK-3 inhibition differentially affects the association of NF-κB p65 and CREB to CBP that regulates the production of IL-10 and IL-12 by LPS-stimulated monocytes. Human monocytes were pre-treated with medium only or 10 μM of SB216763 and then stimulated for the indicated time points with 1 μg/ml of *E. coli* LPS. The ability of *E. coli* LPS in the presence or absence of SB216763 to mediate the degradation and re-synthesis of (A) IκB-α and the phosphorylation of (B) NF-κB p65 (ser 276 or ser 536) were assessed by Western blot. GSK-3 inhibition exhibited a differential effect on the nuclear binding levels of (C) NF-κB p65, (D) NF-κB p50, and (E) CREB (ser133). The interaction of CBP with (F) NF-κB p65 and (G) CREB after treatment of cells with SB216763 (10 μM) were assessed by immunoprecipitation of CBP and probed for (F) NF-κB or (G) CREB levels by immunoblot. (H) To determine the functional effect of GSK-3 regulating CREB activity in LPS-stimulated monocytes, cells were pre-treated for 96 h with medium only, siRNA targeting CREB, or control siRNA and assayed by Western blot for the levels of CREB and total p38. (I, J) Monocytes pre-treated with medium only, siRNA control, or siRNA targeting CREB for 96 h were stimulated with *E. coli* LPS for 20 h and cell-free supernatants assayed by ELISA for the levels of (I) IL-10 and (J) IL-12 p40. To ensure equal protein loading, immunoblots were striped and re-probed with total p38 (A, B, H) or total CBP (F, G). For nuclear extract analysis of (C) NF-κB p65, (D) NF-κB p50, and (E) CREB, optical density values were normalized by loading a standardized amount of protein, as indicated in the figure. * indicates statistical significance at P<0.05. For A, B, E, F, G, H, and I, results are representative of 3 separate experiments. For C and D, results represent the mean±SD of 3 separate experiments.

DETAILED DESCRIPTION OF THE INVENTION

The present invention may be understood more readily by reference to the following detailed description of preferred embodiments of the invention and the Examples included therein and to the Figures and their previous and following description.

DEFINITIONS

As used in the specification and the appended claims, the singular forms "a," "an" and "the" include plural referents unless the context clearly dictates otherwise. Thus, for example, reference to "a small molecule" includes mixtures of one or more small molecules, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

The terms "higher," "increases," "elevates," or "elevation" refer to increases above basal levels, or as compared to a control. The terms "low," "lower," "inhibits," "inhibition," "reduces," or "reduction" refer to decreases below basal levels, or as compared to a control. For example, basal levels are normal in vivo levels prior to, or in the absence of, inflammation or the addition of an agent which causes inflammation.

The term "mediate" or "mediation" and "modulate" or "modulation" means to regulate, or control, in particular to increase, enhance, elevate, or alternatively to lower, inhibit, or reduce. The terms "mediate" and "modulate" are used interchangeably throughout.

"Inflammation" or "inflammatory" is defined as the reaction of living tissues to injury, infection, or irritation. Anything that stimulates an inflammatory response is said to be inflammatory.

"Inflammatory disease" is defined as any disease state associated with inflammation. Examples of inflammatory disease include, but are not limited to, asthma, systemic lupus erythematosus, rheumatoid arthritis, reactive arthritis, spondylarthritis, systemic vasculitis, insulin dependent diabetes mellitus, multiple sclerosis, experimental allergic encephalomyelitis, Sjögren's syndrome, graft versus host disease, inflammatory bowel disease including Crohn's disease, ulcerative colitis, and scleroderma. Inflammatory diseases also includes autoimmune diseases such as myasthenia gravis, Guillain-Barré disease, primary biliary cirrhosis, hepatitis, hemolytic anemia, uveitis, Grave's disease, pernicious anemia, thrombocytopenia, Hashimoto's thyroiditis, oophoritis, orchitis, adrenal gland diseases, anti-phospholipid syndrome, Wegener's granulomatosis, Behcet's disease, polymyositis, dermatomyositis, multiple sclerosis, vitiligo, ankylosing spondylitis, *Pemphigus vulgaris*, psoriasis, dermatitis herpetiformis, Addison's disease, Goodpasture's syndrome, Basedow's disease, thrombopenia purpura, allergy; and cardiomyopathy.

"Infection" or "infectious process" is defined as one organism being invaded by any type of foreign material or another organism. The results of an infection can include growth of the foreign organism, the production of toxins, and damage to the host organism. Infection includes viral, bacterial, parasitic, and fungal infections, for example.

"Liver toxicity" is defined as an abnormal accumulation of toxic substances in the liver. A number of criteria can be used to assess the clinical significance of toxicity data: (a) type/severity of injury, (b) reversibility, (c) mechanism of toxicity, (d) interspecies differences, (e) availability of sensitive biomarkers of toxicity, (e) safety margin (non toxic dose/pharmacologically active dose), and (f) therapeutic potential.

"Cancer therapy" is defined as any treatment or therapy useful in preventing, treating, or ameliorating the symptoms associated with cancer. Cancer therapy can include, but is not limited to, apoptosis induction, radiation therapy, and chemotherapy.

"Transplant" is defined as the transplantation of an organ or body part from one organism to another.

"Transplant rejection" is defined as an immune response triggered by the presence of foreign blood or tissue in the body of a subject. In one example of transplant rejection, antibodies are formed against foreign antigens on the transplanted material.

As used throughout, by a "subject" is meant an individual. Thus, the "subject" can include domesticated animals, such as cats, dogs, etc., livestock (e.g., cattle, horses, pigs, sheep, goats, etc.), laboratory animals (e.g., mouse, rabbit, rat, guinea pig, etc.) and birds. Preferably, the subject is a mammal such as a primate, and, more preferably, a human.

The terms "control levels" or "control cells" are defined as the standard by which a change is measured, for example, the controls are not subjected to the experiment, but are instead subjected to a defined set of parameters, or the controls are based on pre- or post-treatment levels.

GSK-3 and the Inflammatory Response

Glycogen synthase kinase-3 (GSK-3) is a serine/threonine protein kinase that was originally identified as a regulator of glycogen synthase, a key enzyme in glycogen metabolism. GSK-3 is involved in the regulation of a diverse array of cellular functions, including protein synthesis, cell proliferation, cell differentiation, microtubule assembly/disassembly, and apoptosis. GSK-3's substrate specificity is unique in that phosphorylation of substrate only occurs if a phosphoserine or phosphotyrosine is present four residues C-terminal to the site of GSK phosphorylation.

There exist two isoforms of GSK-3, GSK-3α and GSK-3β, and they are strictly regulated via phosphorylation. Phosphorylation of GSK-3β on $Ser^9$ ($Ser^{21}$ in GSK-3α) by protein kinase B (PKB) causes its inactivation and this phosphorylation is the primary mechanism responsible for growth factor inhibition of this kinase. Activation of GSK3-β is dependent upon the phosphorylation of $Tyr^{216}$ ($Tyr^{279}$ in GSK-3α). Upon activation, GSK-3 phosphorylates a number of different cellular proteins, including p53, c-Myc, c-Jun, heat shock factor-1 (HSF-1), nuclear factor of activated T-cells, and cyclin D1. GSK-3 also has been shown to phosphorylate aberrant sites on the microtubule associated protein tau, which is critical for the progression of Alzheimer's disease.

Endotoxin (also known as lipopolysaccharide, or LPS) is a key initiator of the early pro-inflammatory cascade that can mediate host tissue injury and lethal shock. Recognition of conserved microbial products, such as LPS, by the innate immune system leads to a variety of signal transduction pathways. These signal transduction pathways mediate the induction and secretion of cytokines that can regulate the level and duration of an inflammatory response. The systemic inflammatory response that accompanies endotoxic shock is controlled by the levels of pro- and anti-inflammatory cytokines. In this regard, the ability to suppress pro-inflammatory cytolines and/or enhance anti-inflammatory cytokines, i.e. IL-10, reduces the toxic effects of LPS (Berg, 1995; Howard, 1993).

Cytokines are proteins made by cells that affect the behavior of other cells. Cytokines made by lymphocytes are often called lymphokines or interleukins (IL). Cytokines act on specific cytokine receptors on the cells they affect. Binding of the receptor induces activity in the cell such as growth, differentiation, or death. Several cytokines play key roles in mediating acute inflammatory reactions, namely IL-1, TNF-a, IL-6, IL-11, IL-8 and other chemokines, GCSF, and GM-CSF. Of these, IL-1 (α and β) and TNF are extremely potent inflammatory molecules: they are the primary cytokines that mediate acute inflammation induced in animals by intradermal injection of bacterial lipopolysaccharide and two of the primary mediators of septic shock.

Chronic inflammation may develop following acute inflammation and may last for weeks or months, and in some instances for years. During this phase of inflammation, cytokine interactions result in monocyte chemotaxis to the site of inflammation where macrophage activating factors (MAF), such as IFN-g, MCP-1, and other molecules then activate the macrophages while migration inhibition factors (MIF), such as GM-CSF and IFN-g, retain them at the inflammatory site. The macrophages contribute to the inflammatory process by chronically elaborating low levels of IL-1 and TNF which are responsible for some of the resulting clinical symptoms such as anorexia, cachexia, fever, sleepiness, and leukocytosis. The cytokines known to mediate chronic inflammatory processes can be divided into those participating in humoral inflammation, such as IL-3, IL-4, IL-5, IL-6, IL-7, IL-9, IL-10, IL-13, and transforming growth factor-β (TGF-β), and those contributing to cellular inflammation such as IL-1, IL-2, IL-3, IL-4, IL-7, IL-9, IL-10, IL-12, interferons (IFNs), IFN-g inducing factor (IGIF), TGF-β and TNF-α and -β (Feghali et al. Frontiers in Bioscience 2, d12-26, Jan. 1, 1997).

The production of pro-inflammatory cytokines by cells of the innate immune system play an important role in mediating the initial host defense against invading pathogens. Furthermore, the inability to regulate the nature or duration of the host's inflammatory response can often mediate detrimental host effects as observed in chronic inflammatory diseases. For example, in the early stages of sepsis, the host's inflammatory response is believed to be in a hyperactive state with a predominant increase in the production of pro-inflammatory cytokines that mediate host tissue injury and lethal shock. Thus, the ability of the innate immune system to dictate the levels of pro- and anti-inflammatory cytokine production is critical in limiting or modulating the nature of the host inflammatory response.

Toll-like receptors (TLRs) are type I transmembrane proteins involved in innate immunity by recognizing microbial conserved structures. The ability to recognize these microbial structures results in the production of inflammatory mediators that dictate the magnitude and severity of inflammation.

In this regard, sepsis as well as many chronic inflammatory diseases are mediated by an inability to control the inflammatory response.

Upon TLR2-, TLR4-, TLR5-, or TLR9-stimulation, inhibition of GSK-3 resulted in the enhanced production of the anti-inflammatory cytokine, IL-10, by 3 to 6-fold, whereas the levels of pro-inflammatory cytokines including IL-1β, IL-6, IL-12, and IFN-γ were potently reduced by 60 to 90% (Examples 3 and 4). In vivo administration of the GSK-3 inhibitor SB216763 in mice resulted in a severe attenuation of endotoxin lethality when used in either a prophylactic or therapeutic manner. Moreover, analysis of in vivo cytokine production in these mice demonstrated that inhibition of GSK-3 resulted in a profound decrease in the systemic levels of IL-1β, IL-12, and IFN-γ, whereas the levels of IL-10 were increased by more than 2-fold when compared to LPS-treated controls. These findings demonstrate a central role for GSK-3 in differentially controlling the levels of pro- and anti-inflammatory cytokine production upon TLR-stimulation and identify a potential therapeutic target that could serve to modulate the inflammatory response.

Methods of Treatment

An agent that inhibits GSK-3 activity or inhibits phosphorylation of GSK-3 can act in a number of different ways. For example, the agent can mediate phosphorylation of GSK-3 at either the ninth residue of glycogen synthase kinase 3 ($ser^9$) or the twenty-first residue ($ser^{21}$). One example of mediating phosphorylation of GSK-3 is to down-regulate the phosphorylation of GSK-3. Activated Akt is a key physiological mediator of the PI3K pathway due to its ability to subsequently phosphorylate downstream targets, including the phosphorylation and subsequent inhibition of GSK-3 at position $ser^{21}$ (GSK-3α) and $ser^9$ (GSK-3β). Human monocytes stimulated with E. coli LPS exhibited $ser^9$ phosphorylation at multiple time points in which the PI3K inhibitor LY294002 abolished the activity of E. coli LPS to phosphorylate GSK-3.

The agent can also inhibit activity of GSK-3. Phosphorylation on serine 9 or serine 21 can inhibit GSK-3 activity. Reducing phosphorylation of Tyrosine 216 or Tyrosine 279 can also inhibit GSK-3 activity.

Inflammation

Disclosed herein are methods of reducing the severity of inflammation in a subject. These methods include the steps of selecting a subject with inflammation or at risk for inflammation, and administering to the subject an effective amount of an agent that inhibits GSK-3 activity. Specifically, the agent can mediate phosphorylation of GSK-3 on the serine nine residue (GSK-3β) or the serine twenty first residue (GSK-3α). Inhibition of GSK-3 activity or the phosphorylation of GSK-3 ($Ser^9$ or $Ser^{21}$) reduces the severity of inflammation in the subject.

Inflammation can be associated with a number of different diseases and disorders. Examples of inflammation include, but are not limited to, inflammation associated with hepatitis, inflammation associated with the lungs, and inflammation associated with an infectious process. Inflammation can also be associated with liver toxicity, which can be associated in turn with cancer therapy, such as apoptosis induction or chemotherapy, or a combination of the two, for example.

The inflammation can be associated with an inflammatory disease, as disclosed above.

The inflammation can also be associated with cancer. Examples of types of cancer include, but are not limited to, lymphoma (Hodgkins and non-Hodgkins) B-cell lymphoma, T-cell lymphoma, leukemia such as myeloid leukemia and other types of leukemia, mycosis fungoide, carcinoma, adenocarcinoma, sarcoma, glioma, blastoma, neuroblastoma, plasmacytoma, histiocytoma, melanoma, adenoma, hypoxic tumour, myeloma, AIDS-related lymphoma or AIDS-related sarcoma, metastatic cancer, bladder cancer, brain cancer, nervous system cancer, squamous cell carcinoma of the head and neck, neuroblastoma, glioblastoma, ovarian cancer, skin cancer, liver cancer, squamous cell carcinomas of the mouth, throat, larynx, and lung, colon cancer, cervical cancer, breast cancer, cervical carcinoma, epithelial cancer, renal cancer, genitourinary cancer, pulmonary cancer, esophageal carcinoma, head and neck carcinoma, hematopoietic cancer, testicular cancer, colo-rectal cancer, prostatic cancer, and pancreatic cancer.

Activated cells can also be treated at the site of inflammation.

"Activated cells" are defined as cells that participate in the inflammatory response. Examples of such cells include, but are not limited to, T-cells and B-cells, macrophages, NK cells, mast cells, eosinophils, neutrophils, Kupffer cells, antigen presenting cells, as well as vascular endothelial cells.

Infection

Inflammation can be caused by an infectious process in a subject. When the inflammation is associated with an infectious process, the infectious process can be associated with a viral infection. Examples of viral infections include, but are not limited to, Herpes simplex virus type-1, Herpes simplex virus type-2, Cytomegalovirus, Epstein-Barr virus, Varicella-zoster virus, Human herpesvirus 6, Human herpesvirus 7, Human herpesvirus 8, Variola virus, Vesicular stomatitis virus, Hepatitis A virus, Hepatitis B virus, Hepatitis C virus, Hepatitis D virus, Hepatitis E virus, Rhinovirus, Coronavirus, Influenza virus A, Influenza virus B, Measles virus, Polyomavirus, Human Papilomavirus, Respiratory syncytial virus, Adenovirus, Coxsackie virus, Dengue virus, Mumps virus, Poliovirus, Rabies virus, Rous sarcoma virus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B, Rotavirus C, Sindbis virus, Simian Immunodeficiency cirus, Human T-cell Leukemia virus type-1, Hantavirus, Rubella virus, Simian hmnunodeficiency virus, Human immunodeficiency virus type-1, and Human immunodeficiency virus type-2.

When the inflammation is associated with an infectious process, the infectious process can be associated with a bacterial infection. The bacterial infection can be caused by either gram positive or gram negative bacterium. The gram positive bacterium can be selected from the group consisting of: *M. tuberculosis, M. bovis, M. typhinurium, M. bovis* strain BCG, BCG substrains, *M. avium, M. intracellulare, M. africanum, M. kansasii, M. marinum, M. ulcerans, M. avium* subspecies *paratuberculosis, Staphylococcus aureus, Staphylococcus epidermidis, Staphylococcus equi, Streptococcus pyogenes, Streptococcus agalactiae, Listeria monocytogenes, Listeria ivanovii, Bacillus anthracis, B. subtilis, Nocardia asteroides*, and other *Nocardia* species, *Streptococcus viridans* group, *Peptococcus* species, *Peptostreptococcus* species, *Actinomyces israelii* and other *Actinomyces* species, and *Propionibacterium acnes*.

The gram negative bacterium can be selected from the group consisting of: *Clostridium tetani, Clostridium perfringens, Clostridium botulinum*, other *Clostridium* species, *Pseudomonas aeruginosa*, other *Pseudomonas* species, *Campylobacter* species, *Vibrio cholerae, Ehrlichia species, Actinobacillus pleuropneumoniae, Pasteurella haemolytica, Pasteurella multocida*, other *Pasteurella* species, *Legionella pneumophila*, other *Legionella* species, *Salmonella typhi*, other *Salmonella* species, *Shigella* species *Brucella abortus*, other *Brucella* species, *Chlamydi trachomatis*, *Chlamydia psittaci*, *Coxiella burnetti*, *Escherichia coli*, *Neiserria meningitidis*, *Neiserria gonorrhea*, *Haemophilus influenzae*, *Haemophilus ducreyi*, other *Hemophilus* species, *Yersinia pestis*, *Yersinia enterolitica*, other *Yersinia* species, *Escherichia coli*, *E. hirae* and other *Escherichia* species, as well as other *Enterobacteriacae*, *Brucella abortus* and other *Brucella* species, *Burkholderia cepacia*, *Burkholderia pseudomallei*, *Francisella tularensis*, *Bacteroides fragilis*, *Fusobascterium nucleatum*, *Provetella* species and *Cowdria ruminantium*.

The above examples of gram positive and gram negative bacteria are not intended to be limiting, but are intended to be representative of a larger population including all gram positive and gram negative bacteria, as well as non-gram test responsive bacteria. Examples of other species of bacteria include, but are not limited to, *Abiotrophia, Achromnzobacter, Acidaminiococcus, Acidovorax, Acinetobacter, Actinobacillus, Actinobaculum, Actinomadura, Actinoimyces, Aerococcus, Aeromonas, Afipia, Agrobacterium, Alcaligenes, Alloiococcus, Alteromonas, Amycolata, Amycolatopsis, Anaerobospirillum, Anaerorhabdus, Arachnia, Arcanobacterium, Arcobacter, Arthrobacter, Atopobium, Aureobacterium, Bacteroides, Balneatrix, Bartonella, Bergeyella, Bifidobacterium, Bilophila Branhamella, Borrelia, Bordetella, Brachyspira, Brevibacillus, Brevibacterium, Brevundimonas, Brucella, Burkholderia, Buttiauxella, Butyrivibrio, Calymmatobacterium, Campylobacter, Capnocytophaga, Cardiobacterium, Catonella, Cedecea, Cellulomonas, Centipeda, Chlamydia, Chlamydophila, Chromobacterium, Chyseobacterium, Chryseomonas, Citrobacter, Clostridium, Collinsella, Comamonas, Corynebacterium, Coxiella, Cryptobacterium, Delftia, Dermabacter, Dermatophilus, Desulfomonas, Desulfovibrio, Dialister, Dichelobacter, Dolosicoccus, Dolosigranulum, Edwardsiella, Eggerthella, Ehrlichia, Eikenella, Empedobacter; Enterobacter, Enterococcus, Erwinia, Erysipelothrix, Escherichia, Eubacterium, Ewingella, Exiguobacterium, Facklamia, Filifactor, Flavinmonas, Flavobacterium, Francisella, Fusobacterium, Gardnerella, Gemella, Globicatella, Gordona, Haemophilus, Hafnia, Helicobacter, Helococcus, Holdemania Ignavigranum, Johnsonella, Kingella, Klebsiella, Kocuria, Koserella, Kurthia, Kytococcus, Lactobacillus, Lactococcus, Lautropia, Leclercia, Legionella, Leminorella, Leptospira, Leptotrichia, Leuconostoc, Listeria, Listonella, Megasphaera, Methylobacterium, Microbacterium, Micrococcus, Mitsuokella, Mobiluncus, Moellerella, Moraxella, Morganella, Mycobacterium, Mycoplasmia, Myroides, Neisseria, Nocardia, Nocardiopsis, Ochrobactrum, Oeskovia, Oligella, Orientia, Paenibacillus, Pantoea, Parachlamiydia, Pasteurella, Pediococcus, Peptococcus, Peptostreptococcus, Photobacterium, Photorhabdus, Plesiomonas, Porphyrimonas, Prevotella, Propionibacterium, Proteus, Providencia, Pseudomonas, Pseudonocardia, Pseudoramibacter, Psychrobacter; Rahnella, Ralstonia, Rhodococcus, Rickettsia Rochalimaea Roseomonas, Rothia, Ruminococcus, Salmonella, Selenomonas, Serpulina, Serratia, Shewenella, Shigella, Simkania, Slackia, Sphingobacterium, Sphingomonas, Spirillum, Staphylococcus, Stenotrophomonas, Stomatococcus, Streptobacillus, Streptococcus, Streptomyces, Succinivibrio, Sutterella, Suttonella, Tatunella, Tissierella, Trabulsiella, Treponema, Tropheryma, Tsakainurella, Turicella, Ureaplasina, Vagococcus, Veillonella, Vibrio, Weeksella, Wolinella, Xanthomonas, Xenorhabdus, Yersinia*, and *Yokenella.*

When the inflammation is associated with an infectious process, the infectious process can be associated with a parasitic infection. Examples of parasitic infections include, but are not limited to, *Toxoplasma gondii, Plasmodium* species such as *Plasmodium falciparum, Plasmodium vivax, Plasmodium malariae*, and other *Plasmodium* species, *Trypanosoma brucei, Trypanosoma cruzi, Leishmania* species such as *Leishmania major, Schistosoma* such as *Schistosoina mansoni* and other *Shistosoma* species, and *Entamoeba histolytica.*

When the inflammation is associated with an infectious process, the infectious process can be associated with a fungal infection. Examples of fungal infections include, but are not limited to, *Candida albicans, Cryptococcus neoformans, Histoplama capsulatum, Aspergillus fumigatus, Coccidiodes immitis, Paracoccidiodes brasiliensis, Blastoinyces dermitidis, Pneomocystis carnii, Penicillium marneffi*, and *Alternaria alternata.*

Furthermore, the infection can be associated with sepsis. Sepsis, also known as systemic inflammatory response syndrome (SIRS), is a severe illness caused by overwheming infection of the bloodstream by toxin-producing bacteria. Sepsis occurs in 2 of every 100 hospital admissions. It is caused by bacterial infection that can originate anywhere in the body. Common sites include, but are not limited to, the kidneys (upper urinary tract infection), the liver or the gall bladder, the bowel (usually seen with peritonitis), the skin (cellulitis), and the lungs (bacterial pneumonia).

Meningitis may also be accompanied by sepsis. In children, sepsis may accompany infection of the bone (osteomyelitis). In hospitalized patients, common sites of infection include intravenous lines, surgical wounds, surgical drains, and sites of skin breakdown known as decubitus ulcers or bedsores. The infection is often confirmed by a positive blood culture, though blood cultures may be negative in individuals who have been receiving antibiotics. In sepsis, blood pressure drops, resulting in shock. Major organs and systems, including the kidneys, liver, lungs, and central nervous system, stop functioning normally. Sepsis is often life-threatening, especially in people with a weakened immune system or other medical illnesses.

Biological Weapons

Disclosed herein are methods of reducing the severity of inflammation or infection in a subject prior to or after contact with an infectious agent such as a biological weapon. Biological warfare agents include, but are not limited to, bacteria, fingi, and viruses.

Examples of bacteria that can be used in biological warfare include *Bacillus anthracis* (Anthrax), *Chlamyida psittaci* (Ornithosis), *Rickettsia prowaskecki* (typhus), *Vibrio cholerae* (Cholera) *Bartonella quintana* (Trench Fever) *Clostridium botulinum* (Botulism), *Rickettsia rickettsii* (Rocky Mountain Spotted Fever), *Yersinia pestis* (Plague), *Brucella melitensis* (Brucellosis), *Coxiella burnetti* (Q fever), *Rickettsia tsutsugainushii* (Scrub typhus), *Burkholderia mallei* (Glanders), *Francisella tulaensis* (Tularemia), *Salmonella typhi* (Typhoid), *Burkholderia pseudomallei* (Meliodosis), *Rickettsia moonseri* (Typhus), and *Shigella dysenteriae* (Dysentery).

Examples of fungi that can be used as biological warfare agents include, but are not limited to, *Coccidioides immitis* and *Histoplasma capsulatum.*

Examples of viruses that can be used as biological warfare agents include, but are not limited to, viral encephalitis agents, viral hemorrhagic fever agents, Chikuangunya virus, Hantaan virus, Marburg virus, Tick-borne encephalitis virus, Congo-Crimean haemorrhagic fever virus, Japanese encephalitis virus, Monkey pox virus, Variola virus, Dengue fever virus, Junin virus, Omsk hemorrhagic fever virus, Venezuelan equine encephalitis virus, Eastern equine encephalitis virus, Lassa fever virus, Rift valley fever virus, Western equine encephalitis virus, Ebola virus, Lymphocytic choriomeningitis virus, Russian Spring-Summer encephalitis virus, White pox, Equine morbillivirus, Machupo virus, Smallpox virus, and Yellow fever virus.

The agents disclosed herein can be administered to a subject at risk of exposure to a biological warfare agent. For example, the agent can be administered to military troops or those at high risk of exposure to a biological warfare agent. The agent can then prevent or reduce the severity of infection or inflammation in a subject. The agents disclosed herein can be administered to a subject less than 1, 2, 3, 4, 5, 6, 12, 24, 36, or 48 hours, or more, prior to exposure. The agent can also be administered to a subject after the subject has been exposed to a biological warfare weapon. The agents can also be administered to the subject less than 1, 2, 3, 4, 5, 6, 12, 24, 36, or 48 hours, or more, after exposure. When the subject has been exposed prior to treatment, the subject should be treated as quickly as possible after exposure. The agents disclosed herein can be administered in a variety of ways, as disclosed.

Biological Systems

Disclosed are methods of reducing the severity of inflammation in a biological system. These methods can include the steps of selecting an inflamed biological system, or a biological system at risk for inflammation, and administering to the biological system an effective amount of an agent that inhibits GSK-3 or mediates the phosphorylation of GSK-3, inhibition or mediation of phosphorylation of GSK-3 reducing the severity of inflammation in the biological system.

The biological system can comprise an in vitro or ex vivo culture system. If the system comprises an in vitro culture, the culture can be used for screening, for diagnostic purposes, or for the preservation of biological materials If an in vitro culture system is used, the disclosed compositions can be delivered to any type of cell. For example, they can be delivered to any type of mammalian cell. Exemplary types of cells neuron, glia, fibroblast, chondrocyte, osteocyte, endothelial, and hepatocyte.

Biological preservation of organs, tissues and cells are employed in many clinical and veterinary applications wherein living material, is harvested and stored in vitro for some period of time before use. Examples of such applications include organ storage and transplants, autologous and allogeneic bone marrow transplants, whole blood transplants, platelet transplants, cord blood and other stem cell transplants, embryo transfer, artificial insemination, in vitro fertilization, skin grafting and storage of tissue biopsies for diagnostic purposes. Preservation techniques are also important in the storage of cell lines for experimental use in hospital, industrial, university and other research laboratories.

If ex vivo methods are employed, cells or tissues can be removed and maintained outside the body according to standard protocols well known in the art. The biological system can comprise a tissue culture system or an organ culture system.

The agents described herein can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type.

Surgery and Transplantation

Disclosed herein are methods of reducing the severity of inflammation in a subject prior to or after surgery. Inflammation associated with surgery can be caused by an infection, for example. Infections associated with surgery are common, particularly during invasive procedures and those requiring implants, such as joint replacement surgery. Because the immune system is unable to attack bacteria that live on implants, infections can be a serious problem. If an infection of an implant goes untreated, the problem can worsen, and the bacteria can gain such a foothold that can become a systemic problem.

The agents disclosed herein can be administered to a subject less than 1, 2, 3, 4, 5, 6, 12, 24, 36, or 48 hours, or more, prior to surgery. The agents can also be administered to the subject less than 1, 2, 3, 4, 5, 6, 12, 24, 36, or 48 hours, or more, after surgery. The agent can be administered to the subject in a variety of ways, as disclosed herein.

Disclosed are methods of reducing the risk of inflammation in a recipient of an implantation or a transplantation. These methods can include the steps of contacting the implant or transplant with an agent that inhibits GSK-3 activity or mediates the phosphorylation of GSK-3 ($ser^9$ or $ser^{21}$), inhibition of GSK-3 activity or mediation of phosphorylation of GSK-3 reducing the risk of inflammation of the recipient.

Inflammation can be associated with transplant rejection in a transplant or implant recipient. As disclosed above, "transplant rejection" is defined as an immune response triggered by the presence of foreign blood or tissue in the body of a subject. In one example of transplant rejection, antibodies are formed against foreign antigens on the transplanted material. The transplantation can be, for example, tissue, cell or organ transplantation, such as liver, kidney, skin, corneal, pancreas, pancreatic islet cells, eyes, heart, or any other transplantable organ of the body.

Transplantation immunology refers to an extensive sequence of events that occurs after an allograft or a xenograft is removed from a donor and then transplanted into a recipient. Tissue is damaged at both the graft and the transplantation sites. An inflammatory reaction follows immediately, as does activation of biochemical cascades. Such as inflammatory reaction can be reduced using the methods taught herein. In the inflammatory reaction, a series of specific and nonspecific cellular responses ensues as antigens are recognized. Antigen-independent causes of tissue damage (i.e., ischemia, hypothermia, reperfusion injury) are the result of mechanical trauma as well as disruption of the blood supply as the graft is harvested. In contrast, antigen-dependent causes of tissue damage involve immune-mediated damage.

Macrophages release cytokines (e.g., tumor necrosis factor, interleukin-1), which heighten the intensity of inflammation by stimulating inflammatory endothelial responses; these endothelial changes help recruit large numbers of T cells to the transplantation site.

Damaged tissues release pro-inflammatory mediators (e.g., Hageman factor (factor XII) that trigger several biochemical cascades. The clotting cascade induces fibrin and several related fibrinopeptides, which promote local vascular permeability and attract neutrophils and macrophages. The kinin cascade principally produces bradykinin, which promotes vasodilation, smooth muscle contraction, and increased vascular permeability.

Rejection is the consequence of the recipient's alloimmune response to the nonself antigens expressed by donor tissues. In hyperacute rejection, transplant subjects are serologically presensitized to alloantigens (i.e., graft antigens are recognized as nonself). Histologically, numerous polymorphonuclear leukocytes (PMNs) exist within the graft vasculature and are associated with widespread microthrombin formation and platelet accumulation. Little or no leukocyte infiltration occurs. Hyperacute rejection manifests within minutes to hours of graft implantation. Hyperacute rejection has become relatively rare since the introduction of routine pretransplantation screening of graft recipients for antidonor antibodies.

In acute rejection, graft antigens are recognized by T cells; the resulting cytokine release eventually leads to tissue distortion, vascular insufficiency, and cell destruction. Histologically, leukocytes are present, dominated by equivalent numbers of macrophages and T cells within the interstitium. These processes can occur within 24 hours of transplantation and occur over a period of days to weeks.

In chronic rejection, pathologic tissue remodeling results from peritransplant and posttransplant trauma. Cytokines and tissue growth factor induce smooth muscle cells to proliferate, to migrate, and to produce new matrix material. Interstitial fibroblasts are also induced to produce collagen. Histologically, progressive neointimal formation occurs within large and medium arteries and, to a lesser extent, within veins of the graft. Leukocyte infiltration usually is mild or even absent. All these result in reduced blood flow, with subsequent regional tissue ischemia, fibrosis, and cell death. (Prescilla et al. http://www.emedicine.com, Immunology of Transplant Rejection, updated Jun. 20, 2003).

Transplant rejection may occur within 1-10 minutes of transplantation, or within 10 minutes to 1 hour of transplantation, or within 1 hour to 10 hours of transplantation, or within 10 hours to 24 hours of transplantation, within 24 hours to 48 hours of transplantation, within 48 hours to 1 month of transplantation, within 1 month to 1 year of transplantation, within 1 year to 5 years of transplantation, or even longer after transplantation.

The implant or transplant can be contacted with an agent that mediates phosphorylation or inhibits activity of GSK-3 prior to or during implantation or transplantation into the recipient. The implant or transplant can be contacted at least 1, 5, 10, 15, 20, 30, 45, or 60 minutes prior to implantation or transplantation. The implant or transplant can also be contacted at least 2, 3, 4, 5, 10, 12, 24, 36, or 48 hours prior to implantation or transplantation.

The implant or transplant can also be contacted with an agent that mediates phosphorylation or inhibits activity of GSK-3 after implantation or transplantation into the recipient. The implant or transplant can be contacted at least 1, 5, 10, 15, 20, 30, 45, or 60 minutes after implantation or transplantation. The implant or transplant can also be contacted at least 2, 3, 4, 5, 10, 12, 24, 36, or 48 hours after implantation or transplantation.

Compositions and Screening Methods

Disclosed are GSK-3 peptides and nucleic acids that can be used with the methods disclosed throughout the application. Also disclosed are the agents that modulate GSK-3 to be used within the methods disclosed herein, as well as screening methods that allow for identification of these agents. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular compound is disclosed and discussed and a number of modifications that can be made to a number of molecules including the amino acids are discussed, specifically contemplated is each and every combination and permutation of the transgene and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

GSK-3

As discussed above, GSK-3 is a ubiquitously expressed, highly conserved serine/threonine protein kinase that is involved in the signal transduction cascades of multiple cellular processes. There exist two isoforms of GSK-3, GSK-3α (SEQ ID NO: 1) and GSK-3β (SEQ ID NO: 2), and they are strictly regulated via phosphorylation. The nucleic acids of GSK-3α and GSK-3β are represented by SEQ ID NO: 3 and SEQ ID NO: 4, respectfully. Phosphorylation of GSK-3β on $Ser^9$ ($Ser^{21}$ in GSK-3α) by protein kinase B (PKB) causes its inactivation is the primary mechanism responsible for growth factor inhibition of this kinase. Activation of GSK3-β is dependent upon the phosphorylation of $Tyr^{216}$ ($Tyr^{279}$ in GSK-3α).

```
SEQ ID NO: 1 (GSK-3α peptide sequence)
msgggpsggg pggsgrarts sfaepggggg gggggpggsa sgpggtgggk asvgamgggv gasssgggpg gsggggsggp gagtsfpppg vklgrdsgkv ttvvatlgqg persqevayt dikvigngsf gvvyqarlae trelvaikkv lqdkrfknre lqimrkldhc nivrlryffy ssgekkdely lnlvleyvpe tvyrvarhft kakltipily vkvymyqlfr slayihsqgv chrdikpqnl lvdpdtavlk lcdfgsakql vrgepnvsyi csryyrapel ifgatdytss idvwsagcvl aelllgqpif pgdsgvdqlv eiikvlgtpt reqiremnpn ytetkfpqik ahpwtkvfks rtppeaialc sslleytpss rlspleacah sffdelrclg tqlpnnrplp plfnfsagel siqpslnail ipphlrspag tttltpssqa ltetptssdw qstdatptlt nss SEQ ID NO: 2 (GSK-3β peptide sequence)
msgrprttsf aesckpvqqp safgsmkvsr dkdgskvttv vatpgqgpdr pqevsytdtk vigngsfgvv yqaklcdsge lvaikkvlqd krfknrelqi mrkldhcniv rlryffyssg ekkdevylnl vldyvpetvy rvarhysrak qtlpviyvkl ymyqlfrsla yihsfgichr dikpqnllld pdtavlklcd fgsakqlvrg epnvsyicsr yyrapelifg atdytssidv wsagcvlael llgqpifpgd sgvdqlveii kvlgtptreq iremnpnyte fkfpqikahp wtkvfrprtp peaialcsrl
``` leytptarlt pleacahsff delrdpnvkl pngrdtpalf nfttqelssn pplatilipp hariqaaasp panataasdt nagdrgqtnn aasasasnst SEQ ID NO: 3 (GSK-3α nucleic acid sequence)
gcggcgcggc ctggaagagg ccagggcccg ggggaggcgg cggcagcggc ggcggctggg gcagcccggg cagcccgagc cccgcagcct gggcctgtgc tcggcgccat gagcggcggc gggccttcgg gaggcggccc tgggggctcg ggcagggcgc ggactagctc gttcgcggag cccggcggcg gaggcggagg aggcggcggc ggccccggag gctcggcctc cggcccaggc ggcaccggcg gcggaaaggc atctgtcggg gccatgggtg ggggcgtcgg ggcctcgagc tccggggtg acccggcgg cagcggcgga ggaggcagcg gaggcccccgg cgcaggcact agcttcccgc cgcccggggt gaagctgggc cgtgacagcg ggaaggtgac cacagtcgta gccactctag gccaaggccc agagcgctcc caagaagtgg cttacacgga catcaaagtg attggcaatg gctcatttgg ggtcgtgtac caggcacggc tggcagagac caggaaacta gtcgccatca agaaggttct ccaggacaag aggttcaaga accgagagct gcagatcatg cgtaagctgg accactgcaa tattgtgagg ctgagatact ttttctactc cagtggcgag aagaaagacg agctttacct aaatctggtg ctggaatatg tgcccgagac agtgtaccgg gtggcccgcc acttccaccaa ggccaagttg accatcccta tcctctatgt caaggtgtac atgtaccagc tcttccgcag cttggcctac atccactccc agggcgtgtg tcaccgcgac atcaagcccc agaacctgct ggtggaccct gacactgctg tcctcaagct ctgcgatttt ggcagtgcaa agcagttggt ccgaggggag cccaatgtct cctacatctg ttctcgctac taccgggccc cagagctcat ctttggagcc actgattaca cctcatccat cgatgtttgg tcagctggct gtgtactggc agagctcctc ttgggccagc ccatcttccc tggggacagt ggggtggacc agctggtgga gatcatcaag gtgctgggaa caccaacccg ggaacaaatc cgagagatga acccccaacta cacggagttc aagttccctc agattaaagc tcacccctgg acaaaggtgt caaatctcg aacgccgcca gaggccatcg cgctctgctc tagcctgctg gagtacaccc catcctcaag gctctcccca ctagaggcct gtgcgcacag cttctttgat gaactgcgat gtctgggaac ccagctgcct aacaaccgcc cacttccccca tctcttcaac ttcagtgctg gtgaactctc catccaaccc tctctcaacg ccattctcat ccctcctcac ttgaggtccc cagcgggcac taccaccctc accccgtcct cacaagcttt aactgagact ccgaccagct cagactggca gtcgaccgat gccacaccta ccctcactaa ctcctcctga gggccccacc aagcacccctt ccacttccat ctgggagccc caagaggggc tggaagggg ggccatagcc catcaagctc ctgccctggc tgggcccta gactagaggg cagaggtaaa tgagtccctg tccccacctc cagtccctcc ctcaccagcc tcacccctgt ggtgggcttt ttaagaggat tttaactggt tgtggggagg gaagagaagg acagggtgtt gggggggatga ggacctccta ccccccttggc cccctccccct ccccagacc tccacctcct ccagaccccc tccctcctgt gtcccttgt aaatagaacc agcccagccc gtctcctctt cccttccctg gccccggt gtaaatagat tgttataatt ttttttcttaa agaaaacgtc gattcgcacc gtccaacctg gccccgcccc tcctacagct gtaactcccc tcctgtcctc tgccccccaag gtctactccc tcctcacccc accctggagg gccaggggag tggagagagc tcctgatgtc ttagtttcca cagtaaggtt tgcctgtgta cagacctccg ttcaataaat tattggcatg aaaacctgaa aaaaaaaaaa aaaaaaaa SEQ ID NO: 4 (GSK-3β nucleic acid)
atcatctata tgttaaatat ccgtgccgat ctgtcttgaa ggagaaatat atcgcttgtt ttgtttttta tagtatacaa aaggagtgaa aagccaagag gacgaagtct ttttctttt cttctgtggg agaacttaat gctgcattta tcgttaacct aacaccccaa cataaagaca aaaggaagaa aaggaggaag gaaggaaaag gtgattcgcg aagagagtga tcatgtcagg gcggcccaga accacctcct ttgcggagag ctgcaagccg gtgcagcagc cttcagcttt tggcagcatg aaagttagca gagacaagga cggcagcaag gtgacaacag tggtggcaac tcctgggcag ggtccagaca ggccacaaga gtcagctat acagacacta aagtgattgg aaatggatca tttggtgtgg tatatcaagc caaactttgt gattcaggaa actggtcgc catcaagaaa gtattgcagg acaagagatt taagaatcga gagctccaga tcatgagaaa gctagatcac tgtaacatag tccgattgcg ttatttcttc tactccagtg gtgagaagaa agatgaggtc tatcttaatc tggtgctgga ctatgttccg gaaacagtat acagagttgc cagacactat agtcgagcca aacagacgct cccctgtgatt tatgtcaagt gtatatgta tcagctgttc cgaagtttag cctatatcca ttcctttga atctgccatc gggatattaa accgcagaac tcttgttgg atcctgatac tgctgtatta aaactctgtg actttggaag tgcaaagcag ctggtccgag gagaacccaa tgtttcgtat -continued

```
atctgttctc ggtactatag ggcaccagag ttgatctttg gagccactga ttatacctct agtatagatg tatggtctgc tggctgtgtg ttggctgagc tgttactagg acaaccaata tttccagggg atagtggtgt ggatcagttg gtagaaataa tcaaggtcct gggaactcca acaagggagc aaatcagaga aatgaaccca aactacacag aatttaaatt ccctcaaatt aaggcacatc cttggactaa ggattcgtca ggaacaggac atttcacctc aggagtgcgg gtcttccgac cccgaactcc accggaggca attgcactgt gtagccgtct gctggagtat acaccaactg cccgactaac accactggaa gcttgtgcac attcattttt tgatgaatta cgggacccaa atgtcaaact accaaatggg cgagacacac ctgcactctt caacttcacc actcaagaac tgtcaagtaa tccacctctg gctaccatcc ttattcctcc tcatgctcgg attcaagcag ctgcttcaac ccccacaaat gccacagcag cgtcagatgc taatactgga gaccgtggac agaccaataa tgctgcttct gcatcagctt ccaactccac ctgaacagtc ccgagcagcc agctgcacag gaaaaaccac cagttacttg agtgtcactc agcaacactg gtcacgtttg gaaagaatat taaaaaaaaa aaaaaaaaa
```

GSK-3 Modulating Agents

Agents useful with the methods disclosed herein include any agent that can inhibit the activity of GSK-3 or otherwise modulate the phosphorylation of GSK-3. An example of agents that can inhibit the activity of GSK-3 or modulate the phosphorylation of GSK-3 includes lithium chloride, Azakenpaullone, BIO, and SB216763. Another example is Ro31-8220. Compounds related to GSK-3 and lithium chloride that are able to inhibit the activity of GSK-3 or modulate the phosphorylation of GSK-3 can also be used. These agents can first be tested in a screening assay, for example. Other agents not related to lithium chloride and SB216763 can also be identified by screening methods.

Screening methods for identifying compounds are well known in the art, such as those found in U.S. Pat. No. 6,441, 053. An example of a screening method that can be used to identify an inhibitor or modulator of phosphorylation of GSK-3 comprises providing a mixture comprising GSK-3, a source of phosphate, a GSK-3 substrate and a GSK-3 assay buffer, incubating the mixture in the presence or absence of a test compound, and measuring the level of phosphorylation of the GSK-3 substrate. A lower level of phosphorylation of the GSK-3 substrate in the presence of the test compound compared with the level of phosphorylation of the GSK-3 substrate in the absence of the test compound is an indication that the test compound is a GSK-3 inhibitor. Such methods can be used in conjunction with high throughput screens. The GSK-3 inhibitor should also be assessed by detecting a reduction in inflammation or a marker thereof.

In the assay, GSK-3 may be provided as a protein or it may be provided in the assay mixture as an mRNA specifying GSK-3. When the assay comprises cell-free components, GSK-3 is provided as the protein. When the assay is conducted in the milieu of a cell, GSK-3 may be provided as either the protein or as an mRNA specifying GSK-3, wherein, in order that GSK-3 be available in the assay, the mRNA is translated and GSK-3 protein is thereby produced. GSK-3 may also be provided by expression of a plasmid which encodes GSK-3. Standard molecular biology techniques may be used to construct operable plasmids encoding GSK-3 and to express the plasmid in cells (Sambrook, et al., 1989, In: Molecular Cloning: A Laboratory Manual, Cold Spring Harbor Laboratory, New York). Contacting a cell or subject comprising GSK-3, an agent that induces inflammation, and the agent to be tested, and reducing the level of inflammation as compared to a control treated with the agent that induces inflammation indicates an agent that modulates GSK-3 and inflammation.

As discussed herein, the method of identifying a GSK-3 inhibitor can be performed either in vitro wherein the assay mixture is cell-free, in vitro wherein live cells are included in the assay, or in vivo in an animal. Thus, in one aspect of the invention, the mixture is contained within a eukaryotic cell and the method of the invention may be performed wherein some of the components of the assay mixture may be provided exogenously to a cell my microinjection of the components therein, and some of the components may be endogenous in the cell.

When a eukaryotic cell is used, one or more of GSK-3, GSK-3 substrate and the test compound may be injected into the eukaryotic cell prior to the incubation. The cell so injected is then incubated under conditions which facilitate GSK-3 activity and the level of GSK-3 activity is subsequently measured following the incubation period using the assays described herein.

The eukaryotic cell which is useful in the methods of the invention may be any one of a *Xenopus laevis* oocyte, a *Xenopus laevis* embryo cell, a mammalian cell (such as a 10T1/2 cell), a *Drosophila melanogaster* S2 cell, a *Dictyostelium discoideum* cell and a yeast cell. The eukaryotic cell can be a *Xenopus laevis* embryo ventral vegetal blastomere cell.

The source of phosphate for use in the methods of the invention may be any common source of phosphate, including, but not limited to, a nucleotide triphosphates such as, but not limited to, ATP or GTP. The phosphate source can have bound thereon a detectable label which label is transferred with the phosphate group to the GSK-3 substrate during the reaction. In this manner, phosphorylated GSK-3 substrate may be distinguished from non-phosphorylated GSK-3 substrate in that the phosphorylated substrate will contain the detectable label whereas the non-phosphorylated substrate will not contain the label. In another embodiment, the phosphate source does not have bound thereon a detectable label; instead, phosphorylated GSK-3 substrate may be distinguished from non-phosphorylated GSK-3 substrate, for instance by recognition of one form of the substrate, but not the other, by an antibody.

The detectable label can include any known or heretofore unknown detectable label which is transferred to the GSK substrate upon transfer of a phosphate group thereto as a result of GSK-3 activity. Labels which are useful include, but are not limited to, radioactive labels and non-radioactive labels, such as biotin and the like.

The GSK-3 can be any eukaryotic GSK-3. The GSK-3 which is useful includes, but is not limited to, human GSK-3α, human GSK-3β, *Xenopus laevis* GSK-3α, *Xenopus laevis* GSK-3β, bacterially-expressed *Xenopus laevis* GSK-3β, the expression product of the *Drosophila melanogaster* zw3/sgg gene, and the expression product of the *Dictyostelium discoideum* gskA gene.

The test agent used in the method of the invention may include bis-indolyl maleimides and structurally related compounds, staurosporine, derivatives thereof, and structurally-related compounds of a class known to inhibit other protein kinases, particularly those agents known to inhibit protein kinase C or GSK-3 indirectly.

One example of a method of screening a test compound includes using an in vitro or the in vivo assay wherein at least a pair of assay mixtures is provided. The test agent to be screened is added to one assay mixture in each pair, and is not added to the other assay mixture in the pair. GSK-3 activity is determined in each assay mixture of the pair. If the test agent inhibits GSK-3 or modulates its phosphorylation, then GSK-3 activity will be lower in the assay mixture which contains the test agent than in the assay mixture which does not contain the test compound. One skilled in the art will appreciate that it is desirable to screen test compounds using several different concentrations of the test compound in different assay pairs.

To screen a test compound in vivo in an animal, an animal having cells which express GSK-3 is selected. The test compound is administered to at least one animal, and at least one other animal is not administered the test compound. The activity of GSK-3 in each animal may be assessed in numerous ways, including observation of a macroscopic trait which is influenced by the level of GSK-3 activity in the animal, analysis of the composition of a tissue sample, such as a blood sample, which composition is influenced by the level of GSK-3 activity in the animal, measurement of GSK-3 activity in a tissue sample of the animal, and others methods known to those of skill in the art.

The agent can follow the guidelines of "Lipinski's Rule of Five." (Lipinski, 1997). Lipinski's Rule of Five is particularly useful when the goals of compound design are (i) to have less than 5 hydrogen donors, (ii) less than 10 hydrogen bond acceptors, (iii) molecular weight of less than 500 Daltons and (iv) the log of the partition coefficient, P (where P=the concentration of the compound in water divided by the concentration of the compound in 1 octanol) is less than 5. The Lipinski Rule of Five is a useful guideline, however, the composition is not limited to these parameters.

A wide variety of small molecular weight compounds can be used in the screening methods disclosed herein. Such compounds include, but are not limited to, any compositions which are being tested for drug discovery or development. Such compounds include, but are not limited to, nucleic acids including functional nucleic acids, amino acids including peptides and proteins and fragments thereof, and various other chemical compounds. Compounds can be aqueous- or lipid-soluble. Compounds can be dissolved or suspended within solution, or affixed to a solid-support. Solid supports may include, but are not limited to, insoluble polymer beads or a polymeric matrix coated with one or a plurality of individual compounds, or with combinatorial chemistries. Dosages and volumes which are administered in the screening methods can be varied so as to optimize dosages for further studies or to rank compounds as to their toxicity and/or potency. Information resulting from variations in conditions can be used to prioritize chemicals for further study, to delineate the relative toxicities of structurally related chemicals, and/or to identify the proper dose range for subsequent toxicity studies (see e.g., Harris, et al., Fundam. Appl. Toxicol. 19:186-196).

The carbon-carbon backbone of the compounds can be saturated or unsaturated, cyclic or linear. These aforementioned compounds include, but are not limited to, carbohydrates, polyalcohols (e.g., ethylene glycol and glycerol) and polyphenols (e.g., hydroquinones and tetracyclines). Carbohydrate- and polysaccharide-transformed compounds are defined herein so as to include all chemical moieties possessing a saccharide unit or which are transformed from a saccharide. These compounds can also include glycopeptides, glycolipids and other biopolymers (or biomacromolecules) containing saccharides, either in their entirety or as part of the molecular framework. The term carbohydrates merely represent a portion of a much larger family of polyhydroxylated organic compounds. In addition, carbohydrated/polyhydroxylated organic compounds include, but are not limited to: monomeric acyclic compounds (e.g., ethylene glycol, glycerol and 1,2,3-trihydroxy pentane); polymeric acyclic compounds (e.g., di- or tri-ethylene diglycol; monomeric cyclic compounds (e.g., inositol and 1,2,3-trihydroxycyclopentane); polymeric cyclic compounds (e.g., di-inositol); polymeric and monomeric unsaturated compounds (e.g., tetrahydroxy-1,4-quinone) and polyphenols (e.g., tetracyclines) and derivatives, analogs and fragments thereof.

With respect to the generation of small molecular weight compound libraries, the combination of biochemical diversity is often synergistic with the metabolic diversity obtained from the in vivo production of "natural products". Collections of starting compounds, for example peptides, can be administered to cultures of microorganisms. In accord, each microbial strain may potentially create numerous modified peptides or peptide byproducts, thus generating a "metabolite library". Because each of these aforementioned cultures can contain a very complex mixture of metabolites, a highly efficacious method of screening is required (i.e., high throughput screening). An aliquot of the library is incubated with each of the many strains typical of a microorganism fermentation screening program, and the media screened utilizing an HTS-based assay. Furthermore, natural product diversity can be screened by creating a mixture of combinatorially-tagged liposomes; wherein each liposome preferably encapsulates only one member or a simple mixture of a natural product compound library. The libraries which are generated by the methodologies disclosed herein may be screened for GSK-3 modulating activity.

Administration

Disclosed are agents that can inhibit the activity of GSK-3 or modulate, i.e. down-regulate, the phosphorylation of GSK-3 on $Tyr^{216}$ (GSK-3β) or on $Tyr^{279}$ (GSK-3α) or induce or enhance phosphorylation on $ser^9$ (GSK-3β) or $ser^{21}$ (GSK-3α). The agents can be administered in vivo in a pharmaceutically acceptable carrier. By "pharmaceutically acceptable" is meant a material that is not biologically or otherwise undesirable, i.e., the material may be administered to a subject, along with a nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Delivery

The disclosed agents can be delivered to the target cells in a variety of ways. For example, the agents can be delivered through electroporation, or through lipofection, or through calcium phosphate precipitation. The delivery mechanism chosen will depend in part on the type of cell targeted and whether the delivery is occurring for example in vivo or in vitro.

Thus, the agents can comprise, for example, lipids such as liposomes, such as cationic liposomes (e.g., DOTMA, DOPE, DC-cholesterol) or anionic liposomes. Liposomes can further comprise proteins to facilitate targeting a particular cell, if desired. Administration of an composition comprising a compound and a cationic liposome can be administered to the blood afferent to a target organ or inhaled into the respiratory tract to target cells of the respiratory tract. Regarding liposomes, see, e.g., Brigham et al. Am. J. Resp. Cell. Mol. Biol. 1:95-100 (1989); Felgner et al. Proc. Natl. Acad. Sci USA 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

The agents of the present invention can also be administered using methods of delivering exogenous nucleic acids, such as in gene therapy. See, e.g., U.S. Pat. No. 5,399,346, which is incorporated by reference herein in its entirely for the methods of delivery. Primary cells transfected with the gene for the agent of the present invention can additionally be transfected with tissue specific promoters to target specific organs, tissue, grafts, or cells.

Administration of the agents disclosed herein can occur in conjunction with other therapeutic agents. Thus, the agents of the present invention can be administered alone or in combination with one or more therapeutic agents. For example, a subject can be treated with the disclosed agent alone, or in combination with chemotherapeutic agents, antibodies, antivirals, steroidal and non-steroidal anti-inflammatories, conventional immunotherapeutic agents, cytokines, chemokines, and/or growth factors. Combinations may be administered either concomitantly (e.g., as an admixture), separately but simultaneously (e.g., via separate intravenous lines into the same subject), or sequentially (e.g., one of the compounds or agents is given first followed by the second). Thus, the term "combination" or "combined" is used to refer to either concomitant, simultaneous, or sequential administration of two or more agents.

The agents disclosed herein are of benefit to subjects who are experiencing inflammation or are at risk for inflammation. Because the agents disclosed herein reduce the activity of GSK-3, thereby reducing the severity or duration of the inflammation, any subject that can benefit from a reduction in the activity of GSK-3 can be administered the agents disclosed herein.

The compositions comprising an agent disclosed herein in a pharmaceutically acceptable carrier may be administered orally, parenterally (e.g., intravenously), by intramuscular injection, by intraperitoneal injection, transdermally, extracorporeally, topically or the like, although topical intranasal administration or administration by inhalant is typically preferred. As used herein, "topical intranasal administration" means delivery of the compositions into the nose and nasal passages through one or both of the nares and can comprise delivery by a spraying mechanism or droplet mechanism, or through aerosolization of the nucleic acid or vector. The latter may be effective when a large number of animals is to be treated simultaneously. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein in its entirety for the methods taught.

The compositions may be in solution or in suspension (for example, incorporated into microparticles, liposomes, or cells). These compositions may be targeted to a particular cell type via antibodies, receptors, or receptor ligands. The following references are examples of the use of this technology to target specific proteins to given tissue (Senter, et al., Bioconjugate Chem., 2:447-451, (1991); Bagshawe, K. D., Br. J. Cancer, 60:275-281, (1989); Bagshawe, et al., Br. J. Cancer, 58:700-703, (1988); Senter, et al., Bioconjugate Chem., 4:3-9, (1993); Battelli, et al., Cancer Immunol. Immunother., 35:421-425, (1992); Pietersz and McKenzie, Immunolog. Reviews, 129:57-80, (1992); and Roffler, et al., Biochem. Pharmacol, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. In general, receptors are involved in pathways of endocytosis, either constitutive or ligand induced. These receptors cluster in clathlin-coated pits, enter the cell via clathlin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)).

Pharmaceutically Acceptable Carriers

Delivery of the agents disclosed herein can be used therapeutically in combination with a pharmaceutically acceptable carrier. Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

The pharmaceutical composition may be administered in a number of ways depending on whether local or systemic treatment is desired, and on the area to be treated. Administration may be topically (including opthamalically, vaginally, rectally, intranasally), orally, by inhalation, or parenterally, for example by intravenous drip, subcutaneous, intraperitoneal or intramuscular injection. The disclosed compounds can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Therapeutic Uses

The dosage ranges for the administration of the agents disclosed herein are those large enough to produce the desired effect in which the symptoms of the disorder are affected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any contraindications. Dosage can vary, and can be administered in one or more dose administrations daily, for one or several days.

As described above, the agents disclosed herein can be administered together with other forms of therapy. For example, the molecules can be administered with antibodies, antibiotics, or other cancer treatment protocols as described above, or viral vectors. When the agent is in a vector, as described above, the vector containing the nucleic acid for therapeutic purposes can also contain the agent that modulates GSK-3 activity.

Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include GSK-3, an inflammation inducing agent, and a suitable container. The kit can also include combinatorial libraries of small molecules. The kit can also include a screening platform, such as well plates for screening molecules.

The present invention is more particularly described in the following examples, which are intended as illustrative only since numerous modifications and variations therein will be apparent to those skilled in the art.

Throughout this application, various publications are referenced. The disclosures of these publications in their entireties are hereby incorporated by reference into this application in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

EXAMPLES

Example 1

The PI3K Pathway Regulates Pro- vs. Anti-Inflammatory Cytokine Production

Figure 1:
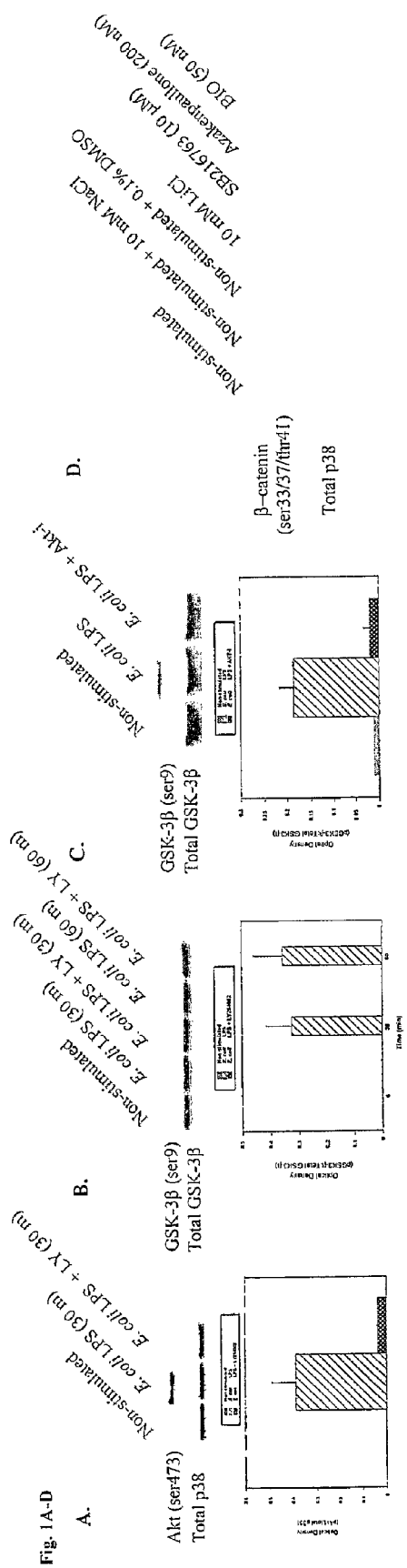
FIG. 1 shows $E.$ $coli$ LPS mediates the activation of (A) Akt ($ser^{473}$) and GSK-3β via the PI3K-Akt pathway in human peripheral blood monocytes. Human monocytes were pre-incubated with medium only, 20 μM LY294002, Akt inhibitor (Akt-i), or inhibitors for GSK-3 (LiCl, SB216763, azakenpaullone, or BIO) for 60 to 90 min before stimulation with 1 μg/ml of $E.$ $coli$ LPS. Control cells were pre-treated (60 to 90 min) with culture media containing 0.01% DMSO (control vehicle for LY294002 and Akt inhibitor) in which no alterations in the phosphorylation of Akt ($ser^{473}$) or GSK-3β ($ser^9$) were observed as compared to monocytes pre-treated with media only and stimulated with $E.$ $coli$ LPS (data not shown). To assess Akt ($ser^{473}$) or GSK-3 ($ser^9$) phosphorylation, 20 μg of total cell lysate was resolved on LDS-PAGE and probed with anti-phospho Akt $Ser^{473}$ or anti-phospho GKS-3 ($ser^9$) followed by ECL detection. Immunoblots were stripped and re-probed with an antibody to total p38 to ensure equal protein loading. Data are representative of 5 separate experiments. * indicates significant differences ($P<0.05$) compared to LPS stimulated cultures.

In an effort to identify if other well-defined TLR-agonists utilize the PI3K pathway to regulate pro- vs. anti-inflammatory cytokine production, as well as identify if a central downstream effector molecule is responsible for mediating the ability of this pathway to differentially dictate the host's inflammatory response, the use of protein-free $E.\ coli$ LPS to stimulate human monocytes in vitro was employed. Activation of PI3K can mediate the recruitment and subsequent activation of signaling proteins possessing pleckstrin homology domains, including the serine-threonine kinase Akt (Franke, 1997; Lawlor, 2001; Stokoe, 1997). After recruitment and activation, Akt becomes phosphorylated at $Thr^{308}$ and $Ser^{473}$ (Franke, 1997; Lawlor, 2001; Stokoe, 1997). Therefore, $E.\ coli$ LPS activation of the PI3K-Akt pathway was assessed (FIG. 1a). Assessment of Akt phosphorylation ($ser^{473}$) demonstrated that $E.\ coli$ LPS mediated the phosphorylation of Akt in which the PI3K inhibitor LY294002 abolished the ability of $E.\ coli$ LPS to induce phosphorylation of Akt (FIG. 1a). Similar results were observed with the ability of $E.\ coli$ LPS to induce the phosphorylation of Akt at $Thr^{308}$.

Previous studies have shown that activated Akt is a key physiologic mediator of the PI3K pathway due to its ability to subsequently phosphorylate downstream targets, including the phosphorylation and subsequent inhibition of the serine/threonine kinase GSK-3 at position $ser^{21}$ (GSK-3β) and $ser^9$ (GSK-3β) (Cross, 1995). Thus, it was investigated if the phosphorylation status of the ubiquitously expressed downstream kinase GSK-3 was being mediated by TLR4-stimulation of human monocytes in a PI3K-Akt-dependent manner. Human monocytes stimulated with *E. coli* LPS exhibited ser$^9$ phosphorylation at multiple time points in which the PI3K inhibitor LY294002 abolished the ability of *E. coli* LPS to phosphorylate GSK-3β (FIG. 1b). A selective Akt inhibitor was then used to determine if this kinase was responsible for the phosphorylation of GSK-3β by *E. coli* LPS (FIG. 1b). The ability of *E. coli* LPS to induce the phosphorylation of GSK-3 (ser$^9$) was dependent upon Akt activity (FIG. 1b). Thus, the ability of the TLR4-signaling pathway to mediate the phosphorylation of GSK-3β occurs via a PI3K-Akt dependent pathway.

In non-stimulated cells, GSK-3 constitutively phosphorylates β-catenin and thus targets β-catenin for degradation. To initially determine the ability of a panel of different GSK-3 inhibitors to inhibit GSK-3 in human monocytes, β-catenin phosphorylation was assessed in the presence or absence of the GSK-3 inhibitors LiCl, SB216763, azakenpaullone, or BIO (FIG. 1D). Non-stimulated monocytes exhibited detectable levels of β-catenin phosphorylation (FIG. 1D). In contrast, monocytes treated with any of the GSK-3 inhibitors tested exhibited no detectable levels of phosphorylated β-catenin (FIG. 1D).

Example 2

Figure 2:
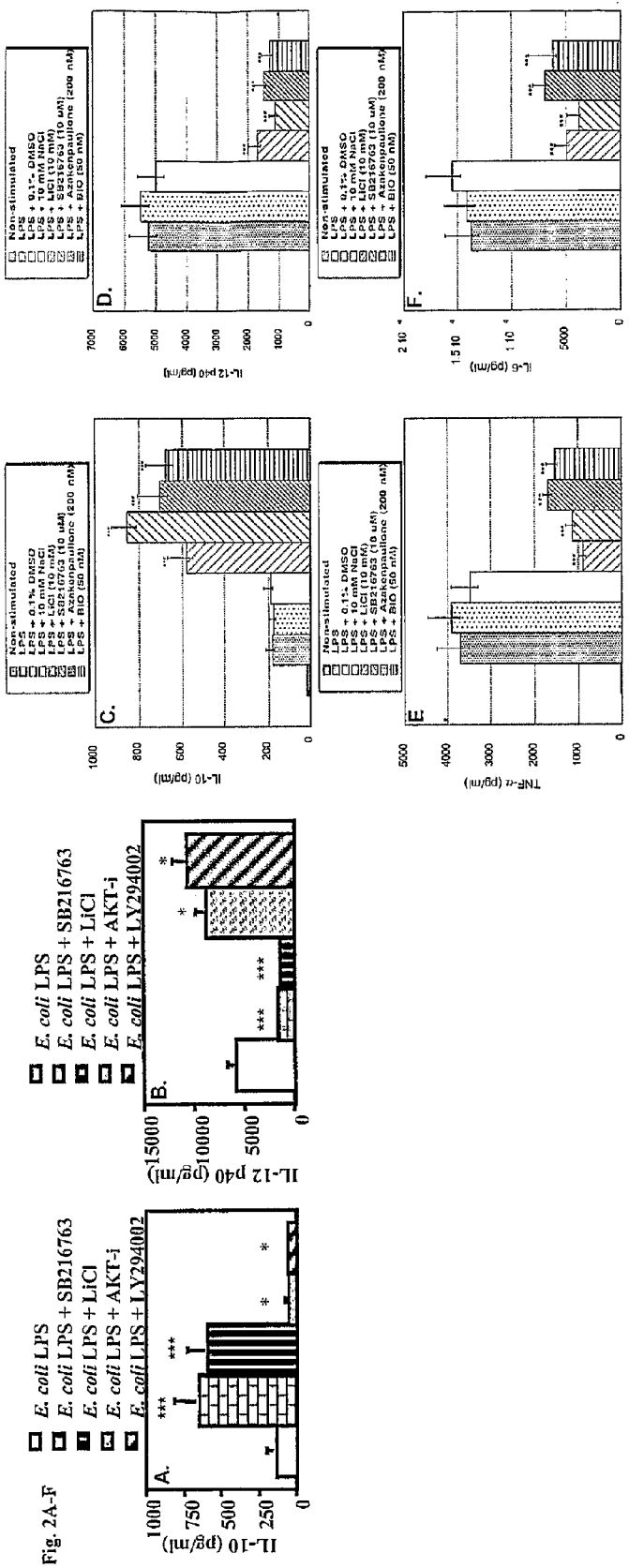
FIG. 2 The ability of the PI3K pathway to differentially modulate the levels of pro- and anti-inflammatory cytokines is mediated by inhibition of GSK-3. Human monocytes were pre-incubated with medium only, 10 μM SB216763, 10 mM LiCl, 200 nM Azakenpaullone, BIO (50 nM), 1 μM Akt-i, or 20 μM LY294002 for 1 h and then stimulated with 1 μg/ml of $E.$ $coli$ LPS for 20 h. Cell-free supernatants were collected and assessed for (A, C) IL-10, (B, D) IL-12 p40, (E) TNF-α, or (F) IL-6 production by ELISA. * and *** indicates significant differences ($P<0.05$ and $P<0.001$, respectively) compared to $E.$ $coli$ LPS stimulated cultures. Results represent the mean±SD of 5 separate experiments.

The Ability of the PI3K Pathway to Mediate the Phosphorylation and Inactivation of GSK-3 (ser$^9$) Differentially Regulates the Ability of the TLR4-Signaling Pathway To identify whether the ability of the TLR4-signaling pathway to engage GSK-3β (ser$^9$) was mediating a functional effect on the production of pro- and anti-inflammatory cytokine production by human monocytes, the levels of IL-10 and IL-12 were assessed in the presence of specific inhibitors for Akt (Akt-i), PI3K (LY294002), and GSK-3 (Lithium chloride, SB216763, Azakenpaullone, and BIO) (FIG. 2). The levels of the anti-inflammatory cytokine IL-10 were increased by 3- to 5-fold when human monocytes were stimulated with *E. coli* LPS in the presence any of the GSK-3 inhibitors (FIG. 2A, 2C). In contrast, inhibition of the PI3K pathway using LY294002 or Akt-i, both of which inhibited the ability of *E. coli* LPS to induce the phosphorylation of GSK-3β (ser$^9$) (FIG. 1B, C), resulted in a severe reduction in IL-10 levels, as compared to *E. coli* LPS-treated monocytes (FIG. 2A). Moreover, assessment of IL-12 p40 production revealed that greater than a 80% reduction in IL-12 p40 levels were observed when human monocytes were stimulated in the presence of the GSK-3 inhibitor LiCl or SB216763 (FIG. 2b). In sharp contrast, IL-12 p40 levels were increased by more than 50% when LY294002 or the AKT inhibitor was employed (FIG. 2B). However, assessment of IL-12 p40 production revealed a greater than 70% reduction when human monocytes were stimulated with LPS in the presence of a GSK-3 inhibitor (FIG. 2B, D). Thus, the ability of the PI3K pathway to mediate the phosphorylation and inactivation of GSK-3 (ser$^9$) differentially regulates the ability of the TLR4-signaling pathway to induce classical pro- and anti-inflammatory cytokines by human monocytes (FIG. 2).

Example 3

The Role of GSK-3 in Differentially Controlling the Levels of Pro- and Anti-Inflammatory Cytokine Production Two members of the protein serine/threonine kinase GSK-3, GSK-3α and GSK-3β, have been shown to be involved in a variety of cellular functions that can be inhibited by LiCl, SB216763, azakenpaullone, or BIO 12-16. However, by using a phospho-specific Ab to GSK-3α/β (ser9/ser21) (FIG. 1B, C), only phosphorylated GSK-3β was detected. Nevertheless, to definitively demonstrate that GSK-3β was responsible for differentially regulating IL-10 and IL-12 levels upon LPS stimulation of human monocytes, we next used small interfering RNA (siRNA) specific for GSK-3β (FIG. 7). GSK-3β silencing by RNA interference for 96 h reduced protein levels of GSK-3β by more than 70%, as compared to non-transfected or siRNA control levels (FIG. 7A). Assessment of IL-10 production by monocytes pre-treated (96 h) with siRNA specific for GSK-3β and subsequently stimulated with *E. coli* LPS, revealed a greater than a two-fold increase in IL-10 levels, as compared to non-transfected or siRNA controls (FIG. 7B). Moreover, IL-12 p40 levels by LPS-stimulated cultures pre-treated (96 h) with siRNA against GSK-3β were reduced by more than 60%, as compared to non-transfected or siRNA controls (FIG. 7C). Taken together, these results demonstrate that GSK-3β is responsible for differentially controlling the levels of IL-10 and IL-12 by LPS-stimulated monocytes.

Figure 3A:
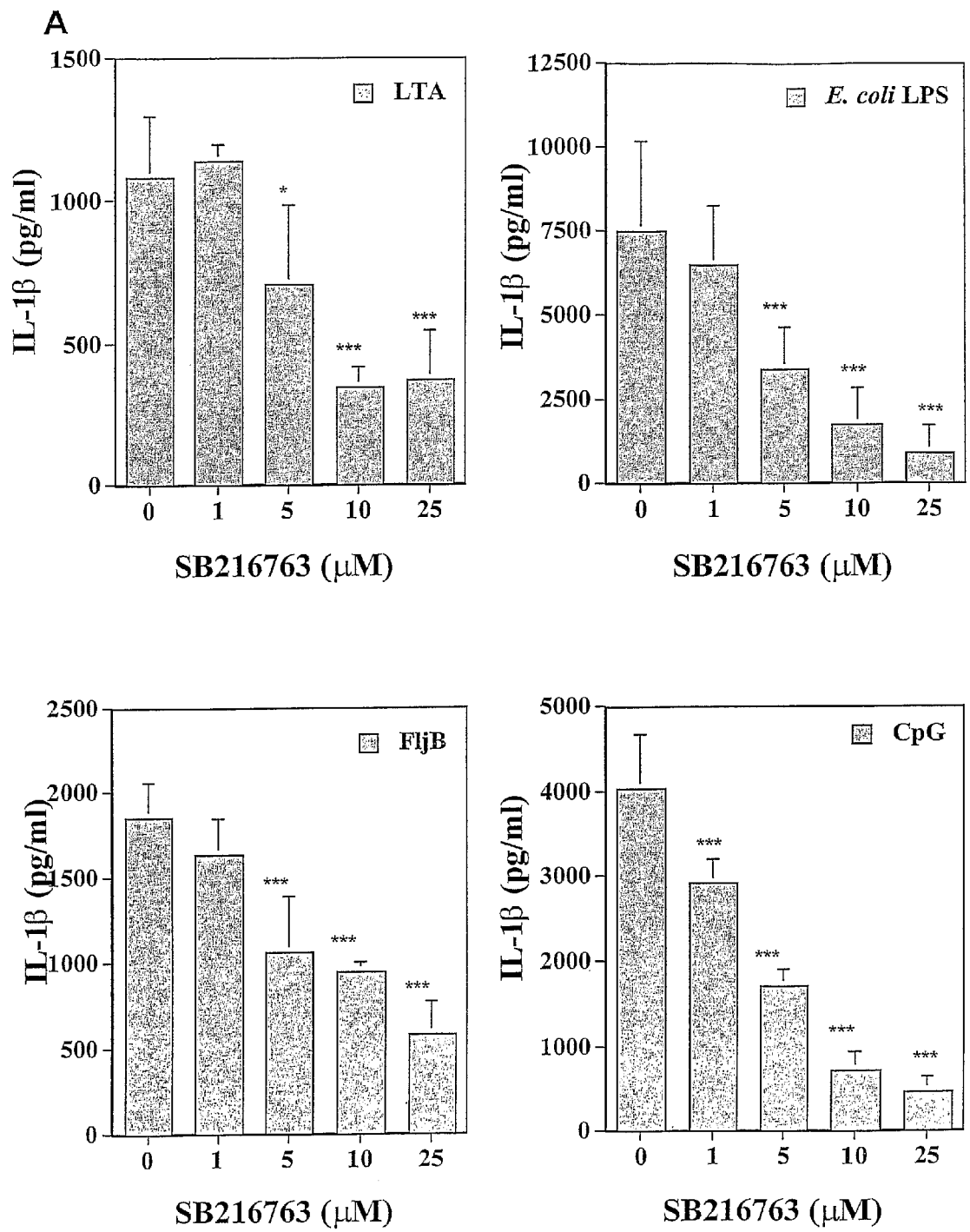
FIG. 3 shows inhibition of GSK-3 differentially regulates the levels of pro-inflammatory and anti-inflammatory cytokine production upon TLR-stimulation of human PBMC. Human PBMC were pre-treated with the indicated concentrations of SB216763 for 60 to 90 min before the addition of a TLR2- (LTA), TLR4- ($E.$ $coli$ synthetic lipid A), TLR5- (flagellin), or TLR9- (CpG) agonist. The levels of (A) IL-1β, (B) IFN-γ, (C) IL-12 p40, (D) IL-6 and (E) IL-10 were determined by ELISA. *, , and * indicate statistical significance at $P<0.05$, $P<0.01$, and $P<0.001$, respectively, as compared to non-treated controls containing 0.01% DMSO. Results represent 8 separate experiments.
Figure 3B:
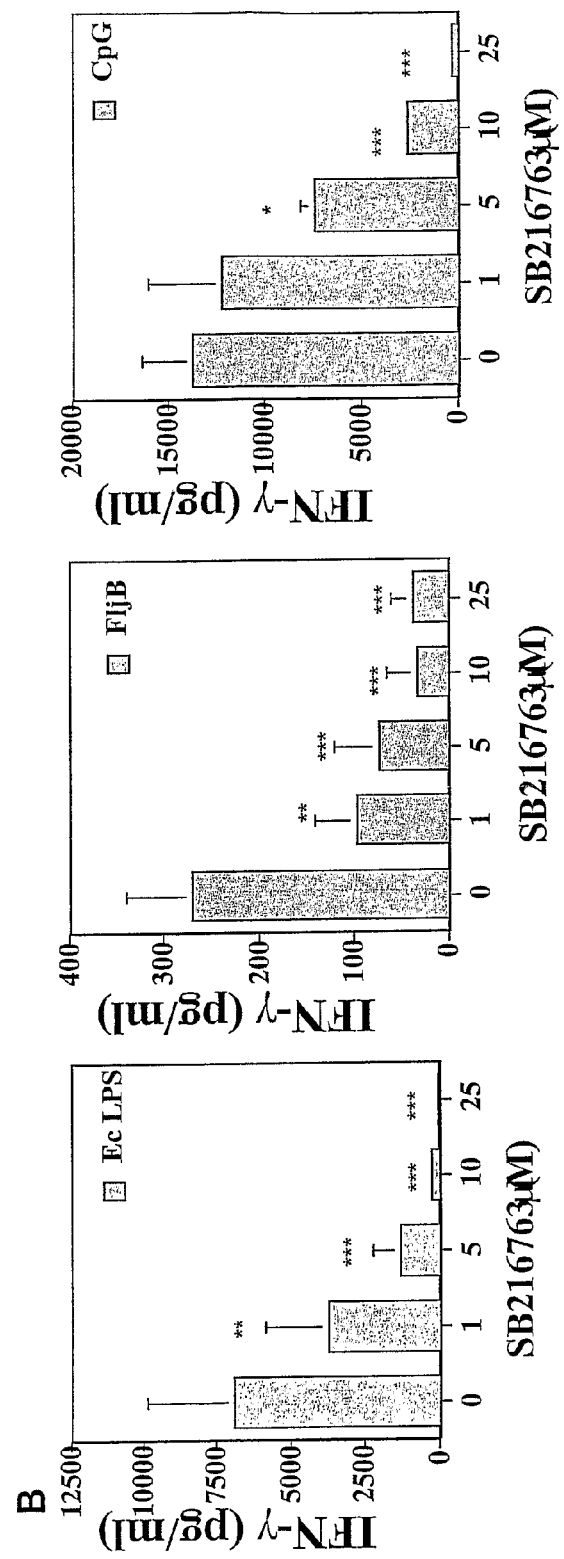
Figure 3C:
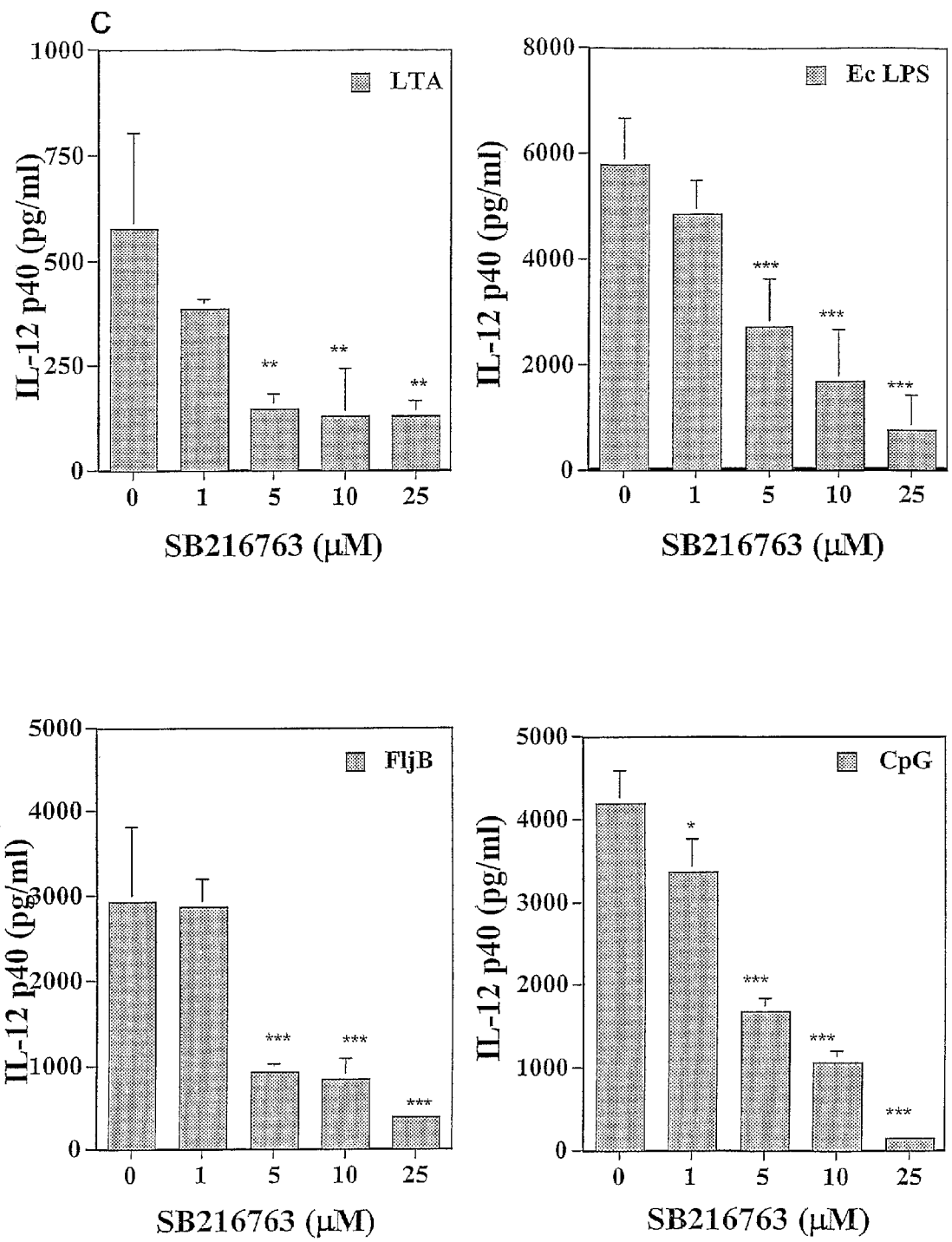
Figure 3D:
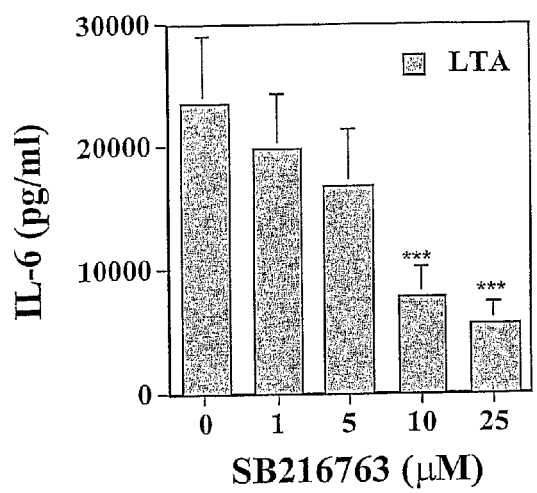
Figure 3D:
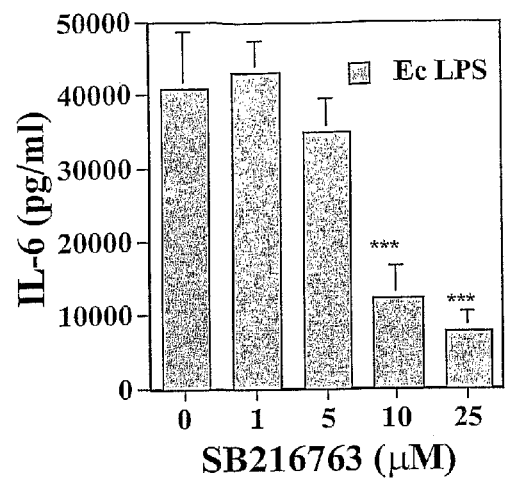
Figure 3D:
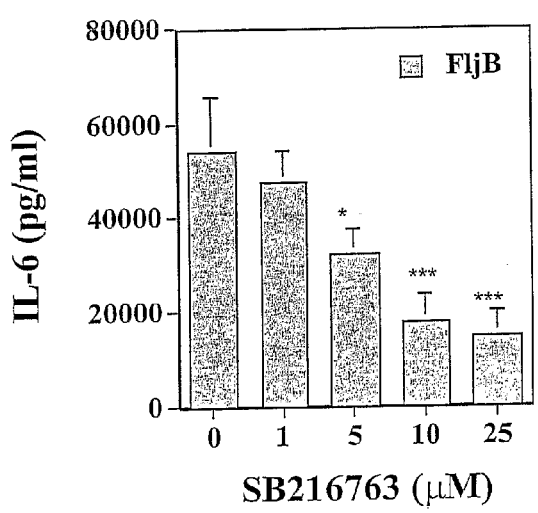
Figure 3D:
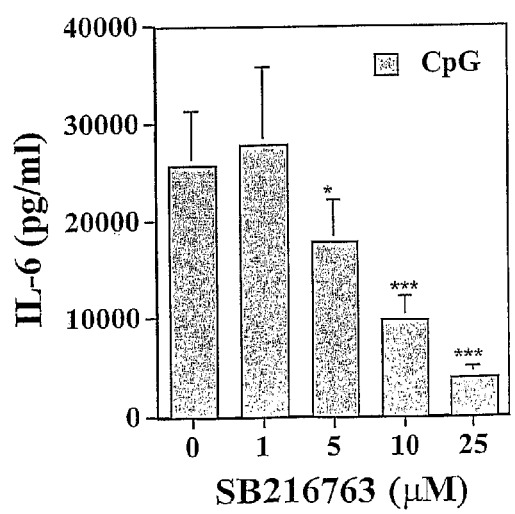
Figure 3E:
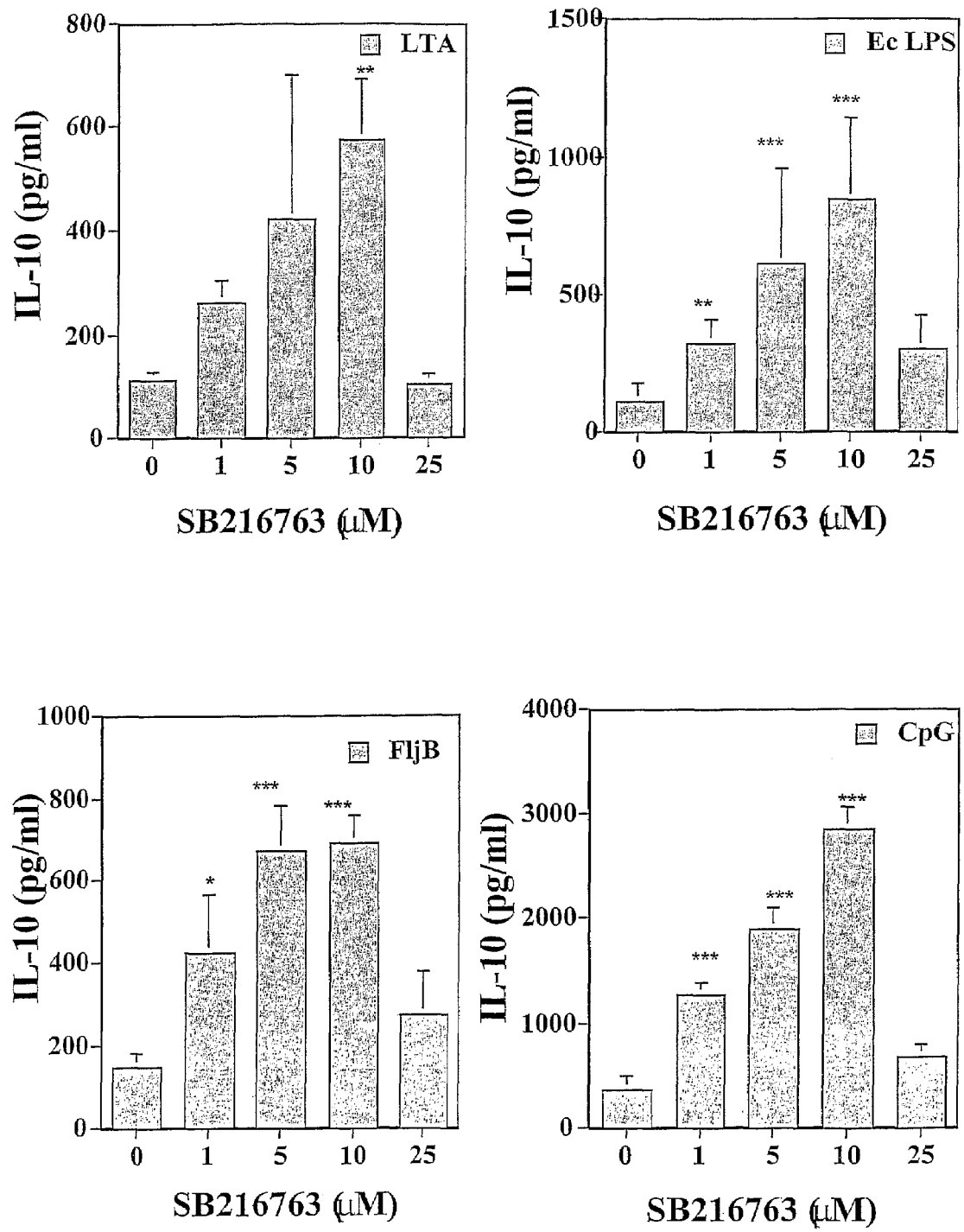

In order to define if the role of GSK-3 in differentially controlling the levels of pro- and anti-inflammatory cytokine production was strictly dependent upon TLR4 or more globally evident among other TLR pathways, selective agonists for TLR2 (LTA from *S. pneumoniae*), TLR4 (synthetic lipid A; Compound 506), TLR5 (flagellin from *S. typhimurium*), and TLR9 (human CpG) were used, and it was assessed how inhibition of GSK-3 in conjunction with a specific TLR-agonist was affecting the inflammatory response by human PBMC. Using the GSK-3 inhibitor SB216763, human PBMC stimulated with TLR2-, TLR4-, TLR5-, or TLR9-agonists exhibited a selective reduction of 50 to 90% (when SB216763 used at 5 to 10 μM) in pro-inflammatory cytokine production, including IL-1, IL-6, IL-12 p40, and IFN-γ (FIGS. 3a-d). In contrast, the levels of the anti-inflammatory cytokine IL-10 were increased by 3 to 8-fold as compared to control-treated cells (FIG. 3e). Similar effects on pro- vs. anti-inflammatory cytokine profiles were also observed in cultures treated with the selective GSK-3 inhibitor LiCl when used at 1 to 10 mM. These data demonstrate that the ability of GSK-3 to selectively regulate the inflammatory response is be well-conserved among the TLR-signaling pathway.

Example 4

GSK-3 and Downstream Transcription Factors

To investigate the underlying cellular mechanism responsible for the ability of GSK-3 inhibition to suppress the production of pro-inflammatory cytokines while concurrently augmenting the production of the anti-inflammatory cytokine IL-10, the ability of how GSK-3 influenced the activation of downstream transcription factors involved in the inflammatory response was assessed. In this regard, past studies have implicated GSK-3 in the regulation of the major eukaryotic transcription factor, nuclear factor κB (NF-κB), which can regulate a diverse number of cellular processes including the regulation of pro-inflammatory cytokine responses. Since the regulation of NF-κB can be mediated at multiple steps, including degradation of the IκB inhibitory molecules, processing of the p105 and p100 molecules, and phosphorylation-dependent association with cellular co-activators including cAMP response element binding protein (CREB)-binding protein (CBP), elucidating what step(s) of the NF-κB pathway could be affected by GSK-3 inhibition was next explored. Analysis of IκB-α degradation induced by *E. coli* LPS was evident at 60 min after exposure (FIG. 9A). The presence of the GSK-3 inhibitor SB216763 failed to alter the rate or extent of degradation or re-synthesis of IκB-α protein (FIG. 9A). Similar results were observed for the degradation and re-synthesis of IκB-α. Since GSK-3 can mediate the phosphorylation of the p65 subunit of NF-κB, it was next determined if GSK-3 inhibition was exerting an effect on the phosphorylation status of the p65 subunit of NF-κB. Neither the level nor duration of p65 phosphorylation (ser276 or ser536) was affected following stimulation of human monocytes with *E. coli* LPS in the presence of the GSK-3 inhibitor SB216763, as compared to cultures stimulated with *E. coli* LPS alone (FIG. 9B). Therefore, the nuclear levels of the NF-κB subunits p50 and p65 were analyzed in the presence or absence of the GSK-3 inhibitor SB216763 (FIG. 9C, D). Nuclear levels of p50 or p65 able to bind its consensus sequence from LPS-stimulated cultures did not appear to be influenced by the presence of SB216763, as compared to monocytes stimulated with LPS alone (FIG. 9C, D).

It has been demonstrated that the optimal transcriptional activity of the p65 subunit of NF-κB is mediated by its association with the nuclear co-activator CBP. Additionally, it has been shown that the nuclear levels of CBP are limiting and the levels of phosphorylated CREB (ser133) and NF-κ p65 (ser276) compete for CBP in which increased association of CREB and CBP have been shown to suppress NF-κB activity. Moreover, it has been shown that GSK-3 can negatively regulate the activation and nuclear binding properties of CREB. Therefore, it was next determined how GSK-3 inhibition was regulating the ability of nuclear CREB (ser133) to bind its consensus sequence (FIG. 9E). The use of the GSK-3 inhibitor SB216763 resulted in a significant increase in the DNA-binding properties of CREB, as compared to monocytes stimulated with LPS alone (FIG. 9E). Since the levels of CREB binding activity were augmented by GSK-3 inhibition, it was determined if GSK-3 inhibition was affecting the ability of CREB (ser133) and NF-κ p65 (ser276) to associate with CBP by co-immunoprecipitation (FIG. 9F, G). LPS-stimulated monocytes showed increases in the levels of both p65 and CREB associated with CBP, as compared to non-stimulated controls (FIG. 9F, G). However, LPS-stimulated cultures that were pre-treated with SB21673 exhibited a pronounced decrease in the levels of p65 associated with CBP (FIG. 9F), whereas the levels of CREB bound to CBP were potently augmented (FIG. 9G). Taken together, these results demonstrate that GSK-3 inhibition results in a differential regulation of the levels of CREB and NF-κB p65 associating with the cellular co-activator CBP.

Past studies characterizing the transcription factors important for IL-10 production in human monocytes have identified CREB as a critical component. Moreover, since it was demonstrated that enhanced levels of CREB were associated with CBP, it was next determined if the ability of GSK-3 inhibition to enhance CREB activity was responsible for differential regulation of pro- and anti-inflammatory cytokine production. Treatment of monocytes with siRNA targeting CREB for 96 hours reduced the level of CREB protein by more than 80%, as compared to non-transfected or siRNA control levels (FIG. 9H). To determine the functional role CREB was mediating in the ability of GSK-3 inhibition to suppress the inflammatory response, the levels of IL-10 from LPS-stimulated monocytes pre-treated (96 h) with siRNA specific for CREB were compared to non-transfected or siRNA controls (FIG. 9I). Cultures pre-treated with SB216763 exhibited an approximate three-fold increase in IL-10 production (FIG. 9I). These levels were similar to those observed in LPS stimulated cultures pre-treated with control siRNA and SB216763 (FIG. 9I). In contrast, LPS stimulated cultures pre-treated with siRNA targeting CREB exhibited a greater than 30% decrease in IL-10 levels, as compared to cultures stimulated with LPS alone or LPS in conjunction with control siRNA (FIG. 9I). Most notably, LPS stimulation of cells pretreated with siRNA targeting CREB and in the presence of the GSK-3 inhibitor SB216763 did not exhibit any discernible increase in IL-10 levels, as compared to LPS stimulated controls (FIG. 9I). In contrast, stimulation of cells pre-treated with siRNA against CREB resulted in an approximate 20% increase in the levels of IL-12 p40, as compared to LPS stimulated or LPS stimulated siRNA controls (FIG. 9J). Pre-treatment of cells with SB216763 resulted in an approximate 80% reduction in the level of IL-12 p40, as compared to LPS or LPS and siRNA controls (FIG. 9J). However, the level of IL-12 p40 observed from LPS-stimulated cultures pre-treated with siRNA (96 h) against CREB did not appear to be altered by the presence of SB216763 (FIG. 9J). These data demonstrate that the ability of GSK-3 to differentially regulate the levels of pro- and anti-inflammatory cytokines by LPS stimulated monocytes is dependent upon regulating CREB activity.

Example 5

Figure 4:
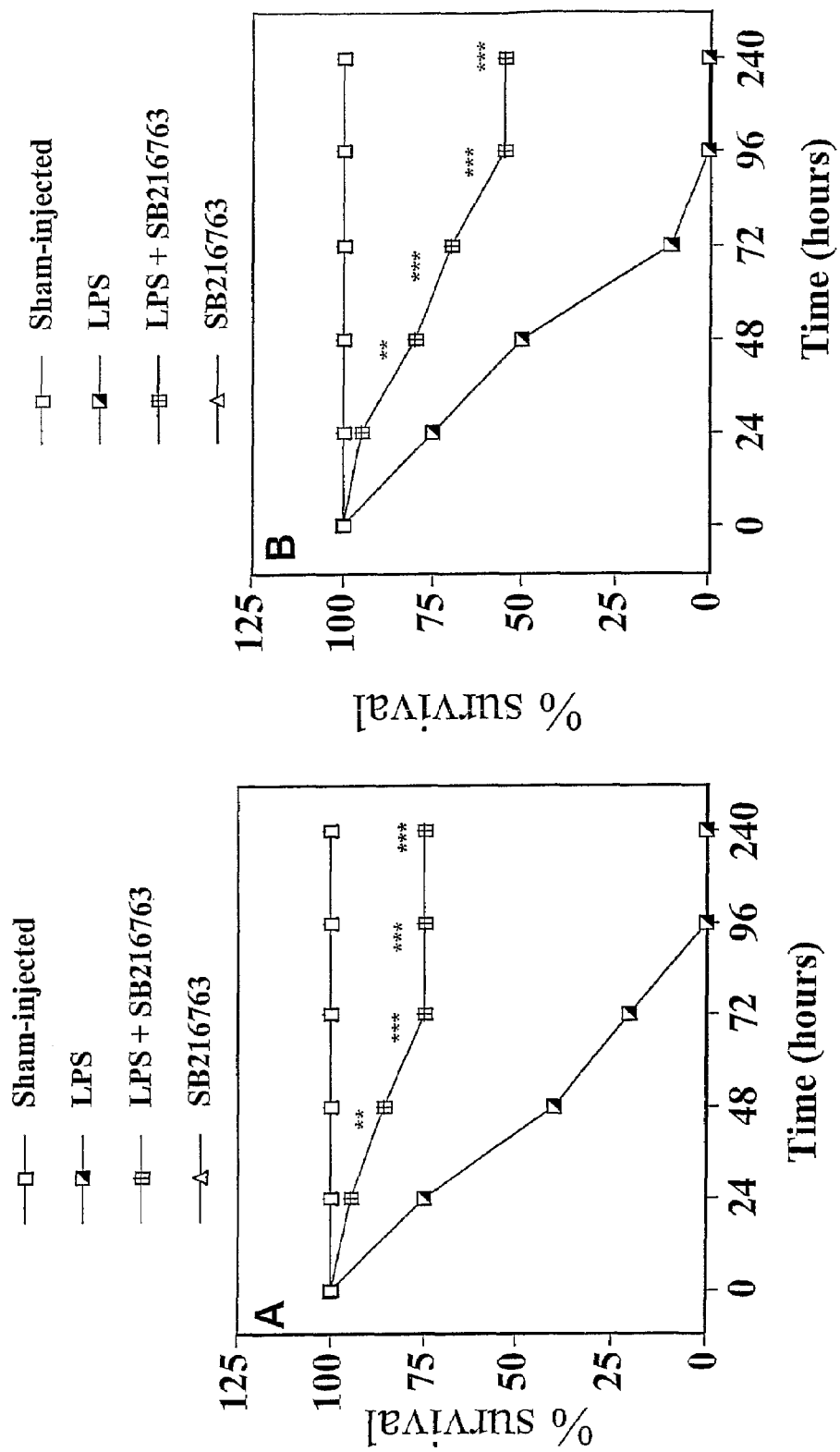
FIG. 4 shows administration of the GSK-3 inhibitor SB216763 mediates protection against LPS lethality in mice when given (A) 2 h before or (B) 2 h after a $LD_{100}$ of LPS. Mice (sham-injected and LPS groups) were pre-treated with i.p. injection of 1 ml PBS containing 0.01% DMSO (vehicle control). SB216763-treated mice were administered 1 ml of PBS containing 30 μM of SB216763. After 2 h, mice pre-treated with SB216763 (denoted LPS+SB216763) or vehicle (denoted LPS group) were given 150 μg of LPS by i.p., injection.  and * indicate statistically significant differences at $P<0.01$ and $P<0.001$, respectively, as compared to LPS-treated group. Results represent the mean of 30 mice/group.
Figure 5:
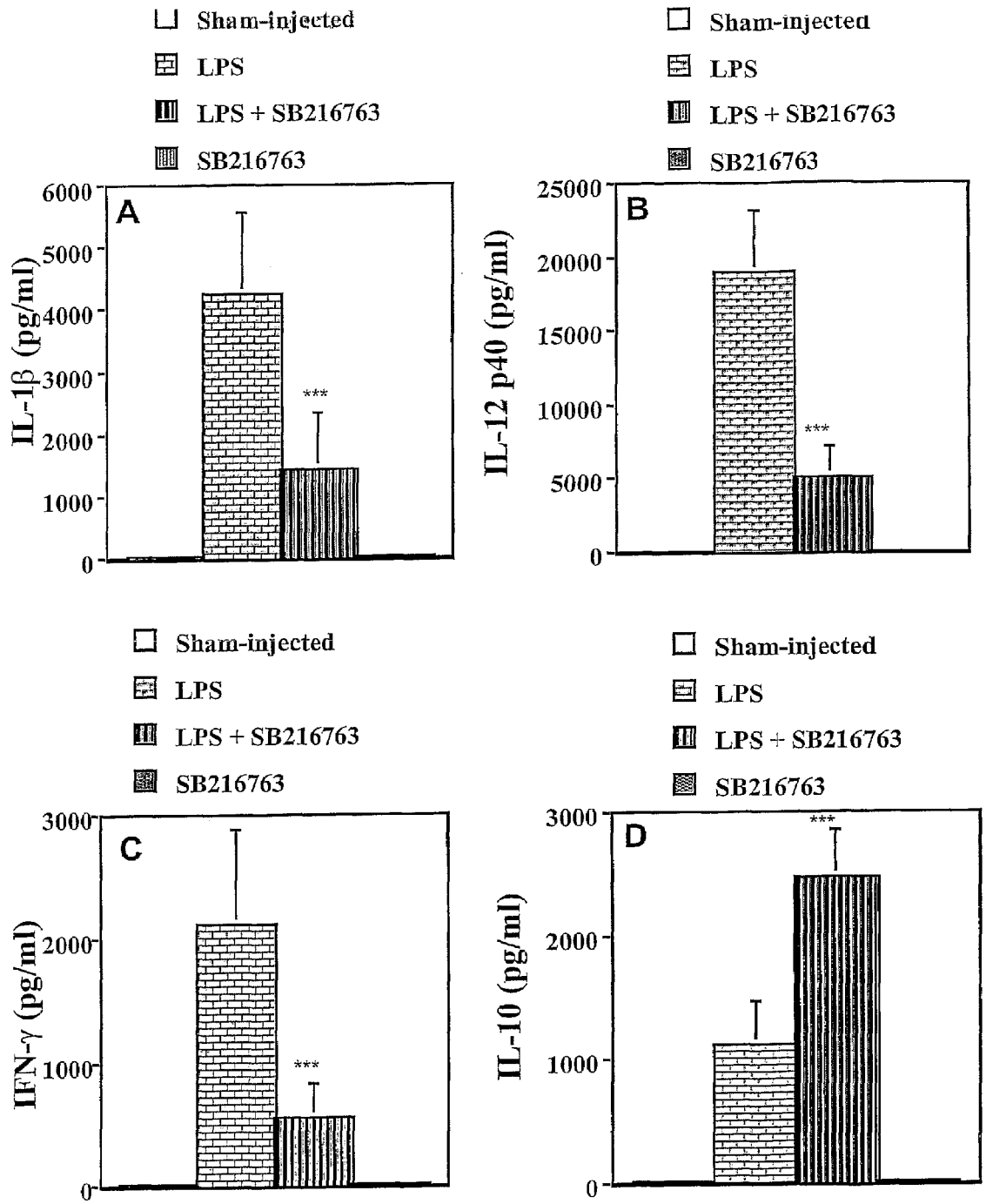
FIG. 5 shows the GSK-3 inhibitor SB216763 suppresses the in vivo production of pro-inflammatory cytokine production including (A) IL-1β, (B) IL-12 p40, and (C) IFN-γ whereas the levels of the anti-inflammatory cytokine (D) IL-10 are enhanced. SB216763-treated mice were given 1 ml of PBS containing 30 μM of SB216763. Sham-injected and LPS groups were given 1 ml of PBS containing vehicle (0.01% DMSO). After 2 h, mice pre-treated with SB216763

Inhibition of GSK-3 In Vivo can Differentially Control Pro- and Anti-Inflammatory Cytokine Production as Well as Protect Mice from the Lethal Effects of LPS Endotoxin is believed to be a key initiator of the early pro-inflammatory cascade that can mediate host tissue injury and lethal shock. The systemic inflammatory response that accompanies endotoxic shock is controlled by the levels of pro- and anti-inflammatory cytokines. In this regard, the ability to suppress pro-inflammatory cytokines and/or enhance anti-inflammatory cytokines, i.e. IL-10, has been shown to severely reduce the toxic effects of endotoxin (Berg, 1995; Howard, 1993). Due to the present findings demonstrating the ability of GSK-3 to differentially control pro- and anti-inflammatory cytokine production, inhibition of GSK-3 in a prophylactic manner was measured to determine if it could mediate protective effects in mice challenged with a lethal dose ($LD_{100}$) of LPS (FIG. 4a). Administration of the GSK-3 inhibitor SB216763 2 hours before a $LD_{100}$ of LPS was given to mice resulted in a severe abrogation of toxicity in which greater than 70% of the mice receiving the GSK-3 inhibitor SB21673 were protected from death, as compared to 0% in control-treated mice (FIG. 4a). Additionally, to investigate if a delayed administration of the GSK-3 inhibitor could be given to mice and still retain efficacy, giving mice SB216763 was delayed until 2 hours after the $LD_{100}$ of LPS (FIG. 4b). The delayed administration of SB216763 resulted in significant protection of mice from LPS-induced death in which approximately 55% of the mice survived, as compared to 0% of the control-treated mice (FIG. 4b). To rule out the possibility that GSK-3 inhibition simply extended the onset of LPS-induced lethality, both groups of mice (FIG. 4a, b) that received the GSK-3 inhibitor SB216763 and survived the $LD_{100}$ of LPS were monitored over a 10-day period in which no late deaths were observed (FIG. 4). Assessment of the pro- and anti-inflammatory cytokine profiles from LPS-challenged mice receiving the $LD_{100}$ of LPS were also determined in order to characterize the nature of the inflammatory response in vivo (FIG. 5). Systemic levels of several pro-inflammatory cytokines were greatly reduced by more than 50% in mice receiving the GSK-3 inhibitor SB216763, as compared to LPS-treated controls (FIGS. 5a-c). In contrast, the in vivo production of IL-10 was increased by more than 2-fold in mice given SB216763, as compared to LPS-treated controls (FIG. 5d). Thus, inhibition of GSK-3 in vivo can differentially control pro- and anti-inflammatory cytokine production as well as protect mice from the lethal effects of LPS when administered in a prophylactic or therapeutic manner.

A central mechanism has been characterized by which the inhibition of GSK-3 differentially affects the nature and magnitude of the inflammatory response. Inhibition of GSK-3 resulted in a profound increase in the levels of the anti-inflammatory cytokine IL-10 upon TLR2-, TLR4-, TLR5-, and TLR9-activation whereas the concurrent production of pro-inflammatory cytokines including IL-1β, IL-12, and IFN-γ were severely reduced by human monocytes and PBMC. These current findings identify a critical role for GSK-3 in modulating pro- vs. anti-inflammatory cytokines in vivo and provide a rationale to regulate the nature and severity of inflammation.

Example 6

General Methods

Mice and Treatment with Endotoxin (LPS)

C57BL/6 mice were bred and maintained within the pathogen-free animal facility at UAB. Experimental endotoxic shock was induced in age- and sex-matched C57BL/6 mice (18 to 23 g) by intraperitoneal injection of 150 µg of LPS in PBS containing 0.1% DMSO. Mice pre-treated with the GSK-3 inhibitor SB216763 received 1 ml of PBS containing 30 µM of SB216763 (DMSO was at 0.01%) by i.p. injection. LPS-control and sham-injected mice were pre-treated (i.p. injection) with 1 ml of PBS containing 0.1% DMSO. Mice given the GSK-3 inhibitor SB216763 after LPS challenge received 1 ml of PBS containing 30 µM of SB216763 (DMSO was at 0.01%) by i.p. injection. LPS-control and sham-injected mice were administered (i.p.) 1 ml of PBS containing 0.01% DMSO. At 4 h after injection, blood from all groups of mice was obtained by retro-orbital plexus bleeding.

Reagents

Protein-free E. coli (K235) LPS were prepared as previously described (Hirschfeld, 2000; Hirschfeld, 2001). Lipoteichoic acid from S. pneumoniae used in the present study was purified as previously described (Han, 2003). Bacterial flagellin (S. typhimurium) was obtained from Dr. Gewirtz (Emory University, Atlanta, Ga.). E. coli synthetic lipid A (Compound 506) was obtained from Dr. Ogawa (Asahi University, Gifu, Japan). CpG (ODN 2216) 5'-ggGGGAC-GATCGTCgggggg-3' (SEQ ID NO: 5) and (ODN 2216 control) 5'-ggGGGAGCATGCTGcggggg-3' (SEQ ID NO: 6) were purchased from InvivoGen. Lithium chloride was purchased from Sigma. The GSK-3 inhibitor SB216763 (Cross, 2001) was obtained from Tocris (Sydney, Australia). The Akt inhibitor II was purchased from Calbiochem (San Diego, Calif.). Antibodies against total p38, Akt (ser473), Akt (thr308), GSK-3β (ser$^9$), and total GSK-3 were purchased from Cell Signaling Technology.

Measurement of Cytokines

Human or mouse IL-1β, IL-10, IL-12 p40, and IFN-γ levels in the plasma of mice or cell-culture supernatants were determined by using enzyme-linked immunosorbent assay (ELISA) kits from R&D systems or Ebioscience according to manufacturer's instructions.

Cell Culture

Heparinized venous blood from healthy donors was used to obtain PBMC by isolating the buffy coat and eliminating RBC contamination by histopaque (SG-1.077) density gradients. Human monocytes were purified from PBMC by negative selection using a monocyte isolation kit purchased from Miltenyi Biotech (Auburn, Calif.). Monocytes were isolated from the PBMC by depletion of non-monocytic cells, which was performed with the aid of an indirect magnetic isolation kit using monoclonal hapten-conjugated CD3, CD7, CD19, CD45RA, CD56, and IgE antibodies (Miltenyi Biotec). This procedure routinely resulted in >95% pure CD14$^+$ cells, as shown by flow cytometry. Human monocytes or PBMC were cultured in 24- ($2\times10^6$/well) or 96- ($2\times10^5$/well) well plates containing RPMI 1640 supplemented with 10% FBS, 50 µM 2-ME, 1 mM sodium pyruvate, 2 mM L-glutamine, 20 mM HEPES, 50 U/ml penicillin, and 50 µg/ml streptomycin. To assess the functional involvement of GSK-3 in TLR-induced cytokine production by monocytes or PBMC, cells were pre-treated for 60 to 90 min with the PI3K inhibitor LY294002, Akt inhibitor II, LiCl, or SB216763 at the indicated concentrations. Control cells were pre-treated with culture media containing 0.01% DMSO (control for LY294002, Akt inhibitor, and SB216763) or 1 to 10 mM of NaCl (control for LiCl).

Endotoxin Shock Model

Male C57BL/6 mice (8 to 12 weeks of age; 18 to 23 g) were injected via the intraperitoneal route with an LD100 (10 g/g) of E. coli K235 LPS in 200 □l of PBS containing 0.1% DMSO. Mice were monitored over a 10 day period for survivability.

Western Blot Analysis

Human monocytes ($2\times10$/ml) in 24-well plates were pre-treated with medium, 0.01% DMSO, Akt-i, LiCl, SB216763, azakenpaullone, and BIO before the addition of medium or LPS. At the indicated time points, cells were washed with PBS and Western blot analysis was performed. Densitometer scans of the blots were performed using the AlphaImager 2000 documentation and analysis system.

NF-κB p50, NF-κB p65, and CREB Activity

Human monocytes in 24-well polystyrene tissue culture plates were pretreated for 1 h with SB216763 or 0.01% DMSO and then incubated with medium alone or LPS for the indicated time points. Cells were collected, washed two times in PBS, and then assayed for activity using the TransAM kit specific for the given transcription factor (Active Motif, Carlsbad, Calif.). The level of nuclear NF-κB p50, NF-κB p65, or CREB was normalized by expressing the optical density emitted at 450 nm from 2 µg NF-κB p50, NF-κ p65, or 20 µg (CREB) of nuclear lysate.

Statistical Analysis

Data were expressed as the mean±SD. Statistical significance between groups was evaluated by ANOVA and the Tukey multiple-comparison test using the InStat program (GraphPad Software). Differences between groups were considered significant at the level of $P<0.05$.

Throughout this application, various publications are referenced. The disclosures of these publications in their entireties are hereby incorporated by reference into this application in order to more fully describe the state of the art to which this invention pertains.

REFERENCES

1. Berg, D. J., K. Kuhn, K. Rajewsky, W. Muller, S. Menon, N. Davidson, G. Grunig, and D. Rennick 1995. Interleukin-10 is a central regulator of the response to LPS in murine models of endotoxic shock and the Shwartzman reaction but not endotoxin tolerance J. Clin. Invest. 96:2339-2347.

2. Cross, D. A., D. R. Alessi, P. Cohen, M. Andjelkovich, and B. A. Hemmings 1995. Inhibition of glycogen synthase kinase-3 by insulin mediated by protein kinase B Nature. 378:785-789.
3. Cross, D. A., A. A. Culbert, K. A. Chalmers, L. Facci, S. D. Skaper, and A. D. Reith 2001. Selective small-molecule inhibitors of glycogen synthase kinase-3 activity protect primary neurones from death J. Neurochem. 77:94-102.
4. Dinarello, C. A. 2000. Proinflammatory cytokines Chest. 118:503-508.
5. Franke, T. F., D. R. Kaplan, L. C. Cantley, and A. Toker 1997. Direct regulation of the Akt proto-oncogene product by phosphatidylinositol-3,4-bisphosphate Science. 275:665-668.
6. Fukao, T., M. Tanabe, Y. Terauchi, T. Ota, S. Matsuda, T. Asano, T. Kadowaki, T. Takeuchi, and S. Koyasu 2002. PI3K-mediated negative feedback regulation of IL-12 production in DCs Nat. Immunol. 3:875-881.
7. Fukao, T., T. Yamada, M. Tanabe, Y. Terauchi, T. Ota, T. Takayama, T. Asano, T. Takeuchi, T. Kadowaki, J. J. Hata, and S. Koyasu 2002. Selective loss of gastrointestinal mast cells and impaired immunity in PI3K-deficient mice. Nat Immunol. 3:295-304.
8. Guha, M., and N. Mackman 2002. The phosphatidylinositol 3-kinase-Akt pathway limits lipopolysaccharide activation of signaling pathways and expression of inflammatory mediators in human monocytic cells J. Biol. Chem. 277: 32124-32132.
9. Han, S. H., J. H. Kim, M. Martin, S. M. Michalek, and M. H. Nahm 2003. Pneumococcal lipoteichoic acid (LTA) is not as potent as staphylococcal LTA in stimulating Toll-like receptor 2 Infect. Immun. 71:541-5548.
10. Hirschfeld, M., Y. Ma, J. H. Weis, S. N. Vogel, and J. J. Weis 2000. Cutting edge: repurification of lipopolysaccharide eliminates signaling through both human and murine toll-like receptor 2 J. Immunol. 165:18-22.
11. Hirschfeld, M., J. J. Weis, V. Toshchakov, C. A. Salkowski, M. J. Cody, D. C. Ward, N. Qureshi, S. M. Michalek, and S. N. Vogel 2001. Signaling by Toll-like receptor 2 and 4 agonists results in differential gene expression in murine macrophages Infect. Immun. 69:1477-1482.
12. Howard, M., T. Muchamuel, S. Andrade, and S. Menon 1993. Interleukin 10 protects mice from lethal endotoxemia J. Exp. Med. 177:1205-1208.
13. Lawlor, M. A., and D. R. Alessi 2001. PKB/Akt: a key mediator of cell proliferation, survival and insulin responses? J. Cell. Sci. 114:2903-2910.
14. Martin, M., R. E. Schifferle, N. Cuesta, S. N. Vogel, J. Katz, and S. M. Michalek 2003. Role of the phosphatidylinositol 3 kinase-Akt pathway in the regulation of IL-10 and IL-12 by *Porphyromonas gingivalis* lipopolysaccharide J. Immunol. 171:717-725.
15. O'Neill, L. A., and C. A. Dinarello 2000. The IL-1 receptor/toll-like receptor superfamily: crucial receptors for inflammation and host defense Immunol. Today. 21:206-209.
16. Stokoe, D. L. R., L. R. Stephens, T. Copeland, R. Piers, J. Gaffney, C. B. Reese, G. F. Painter, A. B. Holmes, F. McCormick, and P. T. Hawkins 1997. Dual role of phosphatidylinositol-3,4,5-trisphosphate in the activation of protein kinase B Science. 277:567-570.
17. Tapping, R. I., S. Akashi, K. Miyake, P. J. Godowski, and P. S. Tobias 2000. Toll-like receptor 4, but not Toll-like receptor 2, is a signaling receptor for *Escherichia* and *Salmonella* lipopolysaccharides J. immunol. 165:5780-5787.
18. Jooss, K. (2003) Gene Ther. 10:955-963; Zaiss, A. K. (2002) J. Virol. 76:4580-4590.
19. Walport, M. J. (2001) N Eng J Med 344:1058-1066 and 1140-1144.
20. Cichon (2001) Gene Ther 8:1794-1800.
21. Feghali et al. Frontiers in Bioscience 2, d12-26, Jan. 1, 1997.
22. Prescilla et al. http://www.emedicine.com, Immunology of Transplant Rejection, updated Jun. 20, 2003.
23. Sambrook, et al., 1989, In: Molecular Cloning: A Laboratory Manual, Cold Spring Harbor Laboratory, New York.
24. Harris, et al., Fundam. Appl. Toxicol. 19:186-196.
25. Brigham et al. Am. J. Resp. Cell. Mol. Biol. 1:95-100 (1989).
26. Felgner et al. Proc. Natl. Acad. Sci USA 84:7413-7417 (1987).
27. U.S. Pat. No. 4,897,355.
28. Senter, et al., Bioconjugate Chem., 2:447-451, (1991).
29. Bagshawe, K. D., Br. J. Cancer, 60:275-281, (1989).
30. Bagshawe, et al., Br. J. Cancer, 58:700-703, (1988).
31. Senter, et al., Bioconjugate Chem., 4:3-9, (1993).
32. Battelli, et al., Cancer Immunol. Immunother., 35:421-425, (1992).
33. Pietersz and McKenzie, Immunolog. Reviews, 129:57-80, (1992); and Roffler, et al., Biochem. Pharmacol, 42:2062-2065, (1991)/
34. Brown and Greene, DNA and Cell Biology 10:6, 399-409 (1991).
35. Doble, B. W. & Woodgett, J. R. GSK-3: tricks of the trade for a multi-tasking kinase. J Cell Sci. 116, 1175-1186 (2003).
36. Stambolic, V., Ruel, L. & Woodgett, J. R. Lithium inhibits glycogen synthase kinase-3 activity and mimics wingless signalling in intact cells. Curr. Biol 6, 1664-1668 (1996).
37. Meijer, L. et al. GSK-3-selective inhibitors derived from Tyrian purple indirubins. Chem. Biol. 10, 1255-1266 (2003).
38. Kunick, C., Lauenroth, K., Leost, M., Meijer, L. & Lemcke, T. 1-Azakenpaullone is a selective inhibitor of glycogen synthase kinase-3 beta. Bioorg. Med. Chem. Lett. 19, 413-416 (2004).
39. Klein, P. S. & Melton, D. A. A molecular mechanism for the effect of lithium on development. Proc. Natl. Acad. Sci. USA 93, 8455-8459 (1996).
40. Hoeflich, K. P. et al. Requirement for glycogen synthase kinase-3beta in cell survival and NF-kappaB activation. Nature 406, 86-90 (2000).
41. Demarchi, F., Bertoli, C., Sandy, P. & Schneider, C. Glycogen synthase kinase-3 beta regulates NF-kappa B1/p105 stability. J. Biol. Chem. 278, 39583-39590 (2003).
42. Demarchi, F., Verardo, R., Varnum, B., Brancolini, C. & Schneider, C. Gas6 anti-apoptotic signaling requires NF-kappa B activation. J. Biol. Chem. 276, 31738-31744 (2001).
43. Nemeth, Z. H. et al. Lithium induces NF-kappa B activation and interleukin-8 production in human intestinal epithelial cells. J. Biol. Chem. 277, 7713-7719 (2002).
44. Schwabe, R. F. & Brenner, D. A. Role of glycogen synthase kinase-3 in TNF-alpha-induced NF-kappaB activation and apoptosis in hepatocytes. Am J Physiol Gastrointest Liver Physiol. 283, G204-G211 (2002).
45. Ghosh, S., May, M. J. & Kopp, E. B. NF-☐B and rel proteins: evolutionary conserved mediators of immune responses. Annu. rev. Immunol. 16, 225-260 (1998).
46. Sheppard, K. A. et al. Transcriptional activation by NF-kappaB requires multiple coactivators. Mol. Cell Biol. 19, 6367-6378 (1999).

47. Zhong, H., Voll, R. E. & Ghosh, S. Phosphorylation of NF-kappa B p65 by PKA stimulates transcriptional activity by promoting a novel bivalent interaction with the coactivator CBP/p300. Mol. Cell 1, 661-671 (1998).

48. Parker, D. et al. Phosphorylation of CREB at Ser-133 induces complex formation with CREB-binding protein via a direct mechanism. Mol. Cell Biol. 16, 694-703 (1996).

49. Grimes, C. A. & Jope, R. S. CREB DNA binding activity is inhibited by glycogen synthase kinase-3 beta and facilitated by lithium. J. Neurochem. 78, 1219-1232 (2001).

50. Platzer, C. et al. Cyclic adenosine monophosphate-responsive elements are involved in the transcriptional activation of the human IL-10 gene in monocytic cells. Eur. J. Immunol. 29, 3098-3104 (1999).

51. Hirschfeld, M., Ma, Y., Weis, J. H., Vogel, S. N. & Weis, J. J. Cutting edge: repurification of lipopolysaccharide eliminates signaling through both human and murine toll-like receptor 2. J. Immunol. 165, 18-22 (2000).

52. Parry, G. C. & Mackman, N. Role of cyclic AMP response element-binding protein in cyclic AMP inhibition of NF-kappaB-mediated transcription. J. Immunol. 159, 5450-5456 (1997).

What is claimed is:

1. A method of treating endotoxic shock, comprising administering an effective amount of GSK-3 inhibitor to a subject having endotoxic shock, wherein the inhibitor is lithium or a pharmaceutically acceptable salt thereof.

2. The method of claim 1, wherein the GSK-3 inhibitor is administered systemically.

3. The method of claim 1, wherein the administration is selected from the group consisting of topical, ophthalmic, vaginal, rectal, intranasal, oral, inhalation, parenteral, intravenous, intraperitoneal, intramuscular, subcutaneous, intracavity, and transdermal routes.

4. The method of claim 1, wherein the pharmaceutically acceptable salt is lithium chloride.

5. The method of claim 1, wherein the endotoxic shock is caused by gram negative bacterial infection.

6. The method of claim 5, wherein the bacterial infection is caused by bacteria selected from the group consisting of: *Clostridium tetani, Clostridium perfringens, Clostridium botulinum, Clostridium* species, *Pseudomonas aeruginosa, Pseudomonas* species, *Campylobacter* species, *Vibrio cholerae, Ehrlichia* species, *Actinobacillus pleuropneumoniae, Pasteurella haemolytica, Pasteurella multocida, Pasteurella* species, *Legionella pneumophila, Legionella* species, *Salmonella typhi, Salmonella* species, *Shigella* species, *Brucella abortus, Brucella* species, *Chlamydia trachomatis, Chlamydia psittaci, Coxiella burnetti, Escherichia coli, Neiserria meningitidis, Neiserria gonorrhea, Haemophilus influenzae, Haemophilus ducreyi, Hemophilus* species, *Yersinia pestis, Yersinia enterolitica, Yersinia* species, *Escherichia hirae, Escherichia* species, Enterobacteriacae, *Burkholderia cepacia, Burkholderia pseudomallei, Francisella tularensis, Bacteroides fragilis, Fusobascterium nucleatum, Provetella* species, and *Cowdria ruminantium*.

7. The method of claim 5, wherein the GSK-3 inhibitor is administered to a subject at a time selected from the group consisting of at least 1 hour, at least 2 hours, at least 3 hours, at least 4 hours, at least 5 hours, at least 6 hours, at least 12 hours, at least 24 hours, at least 36 hours, and at least 48 hours after infection.

8. A method of treating septic shock in a surgery patient, comprising administering an effective amount of GSK-3 inhibitor to the surgery patient, wherein the inhibitor is lithium or a pharmaceutically acceptable salt thereof.

9. The method of claim 8, wherein the GSK-3 inhibitor is administered systemically.

10. The method of claim 8, wherein the administration is selected from the group consisting of topical, ophthalmic, vaginal, rectal, intranasal, oral, inhalation, parenteral, intravenous, intraperitoneal, intramuscular, subcutaneous, intracavity, and transdermal routes.

11. The method of claim 8, wherein the pharmaceutically acceptable salt is lithium chloride.

12. The method of claim 8, wherein the GSK-3 inhibitor is administered to a subject at a time selected from the group consisting of at least 1 hour, at least 2 hours, at least 3 hours, at least 4 hours, at least 5 hours, at least 6 hours, at least 12 hours, at least 24 hours, at least 36 hours, and at least 48 hours after surgery of the patient.

13. The method of claim 8, wherein the GSK-3 inhibitor is administered to a subject at a time selected from the group consisting of at least 1 hour, at least 2 hours, at least 3 hours, at least 4 hours, at least 5 hours, at least 6 hours, at least 12 hours, at least 24 hours, at least 36 hours, and at least 48 hours prior to surgery of the patient.

* * * * *